United States Patent [19]

Chien et al.

[11] Patent Number: 5,042,975
[45] Date of Patent: Aug. 27, 1991

[54] IONTOTHERAPEUTIC DEVICE AND PROCESS AND IONTOTHERAPEUTIC UNIT DOSE

[75] Inventors: Yie W. Chien, North Brunswick, N.J.; John Kong-Jiann Li, Plainsboro, N.J.; Jue-Chen Liu, East Brunswick; Wei-Min Shi; Ovais Siddiqui, both of Piscataway, N.J.; Ying Sun, King of Prussia, Pa.

[73] Assignee: Rutgers, The State University of New Jersey, New Brunswick, N.J.

[21] Appl. No.: 46,984

[22] Filed: May 7, 1987

Related U.S. Application Data

[63] Continuation-in-part of Ser. No. 890,702, Jul. 25, 1986, abandoned.

[51] Int. Cl.⁵ .............................................. A61N 1/30
[52] U.S. Cl. ....................................... 604/20; 128/803
[58] Field of Search ................. 604/20, 50; 128/802, 128/803, 798, 423 R

[56] References Cited

U.S. PATENT DOCUMENTS

| | | | |
|---|---|---|---|
| 3,077,884 | 2/1963 | Batrow et al. | 128/423 R |
| 3,163,166 | 12/1964 | Brant et al. | 104/20 |
| 4,141,359 | 2/1979 | Jacobsen et al. | 604/20 |
| 4,149,533 | 4/1979 | Ishikawa et al. | 604/20 |
| 4,383,529 | 5/1983 | Webster | 604/20 |
| 4,403,984 | 9/1983 | Ash et al. | 604/50 |
| 4,462,274 | 11/1983 | Jacobsen et al. | 604/20 |
| 4,474,570 | 10/1984 | Ariura et al. | 604/20 |
| 4,708,716 | 11/1987 | Sibalis | 604/20 |
| 4,764,164 | 8/1988 | Sasaki | 604/20 |
| 4,786,277 | 11/1988 | Powers et al. | 104/20 |

FOREIGN PATENT DOCUMENTS

| | | | |
|---|---|---|---|
| 2502015 | 9/1982 | France | 604/20 |
| 936928 | 6/1982 | U.S.S.R. | 604/20 |
| 1088730 | 4/1985 | U.S.S.R. | 604/20 |

OTHER PUBLICATIONS

Journal of Controlled Release, 4(1986) 79-85 Keiichiro Okabe et al.

*Primary Examiner*—Lee S. Cohen
*Attorney, Agent, or Firm*—Leroy G. Sinn

[57] ABSTRACT

This invention relates to development of an iontotherapeutic device for regulated transdermal systemic administration of ionizable pharmaceutical compounds.

It also provides an iontotherapeutic process for transdermal administration of ionized pharmaceuticals, particularly those which are otherwise transdermally absorbed to a small degree or not all, such as peptide pharmaceuticals, for example, insulins. The invention also relates to unit dose forms, for example, those in which an ionized pharmaceutical is dispersed in a hydrophilic polymer. The unit dose is adapted to be assembled as part of the pharmaceutical reservoir electrode, so that the ionized pharmaceutical will be delivered transdermally and then be absorbed systemically when the iontotherapeutic device is in operation.

47 Claims, 30 Drawing Sheets

TRANSDERMAL PERIODIC IONTO-THERAPEUTIC SYSTEM
(TPIS)

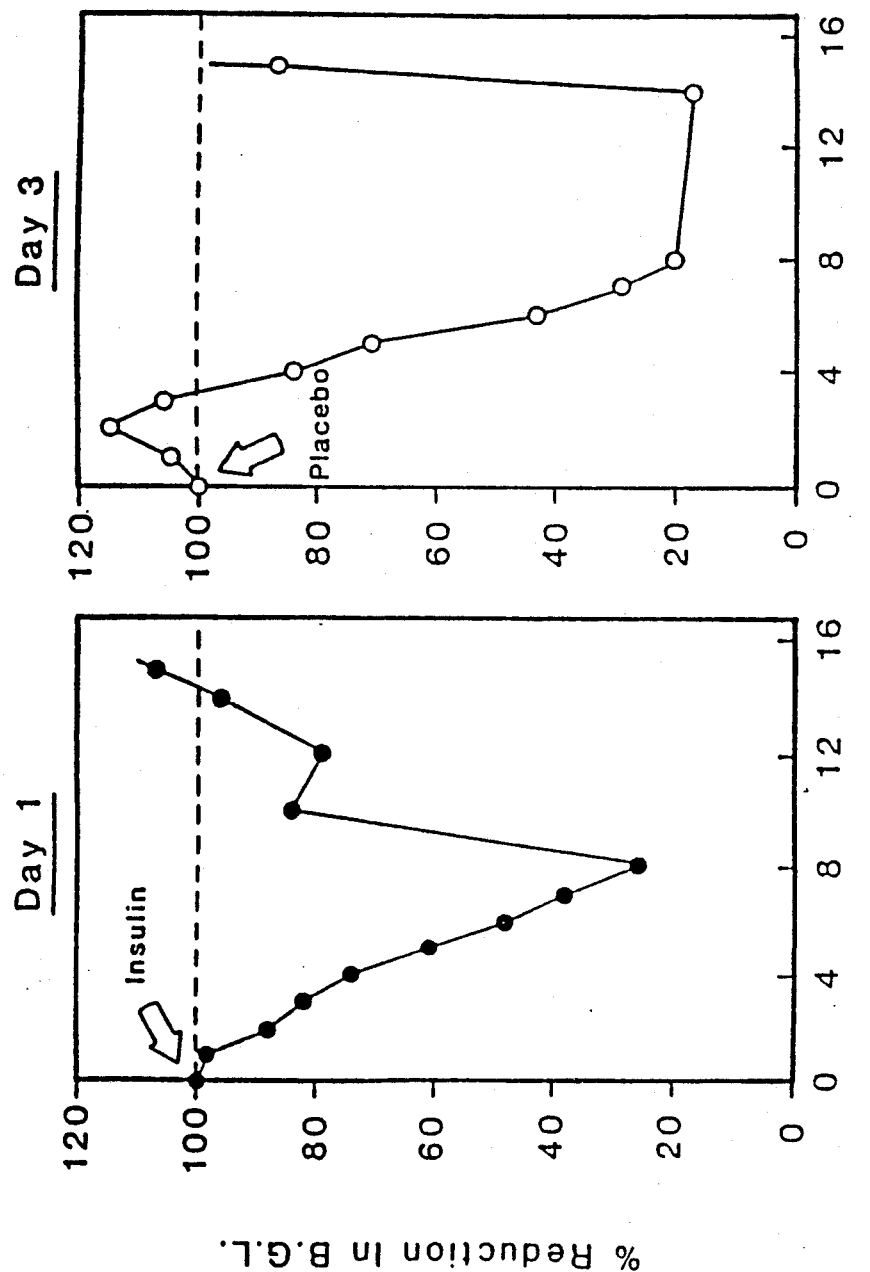

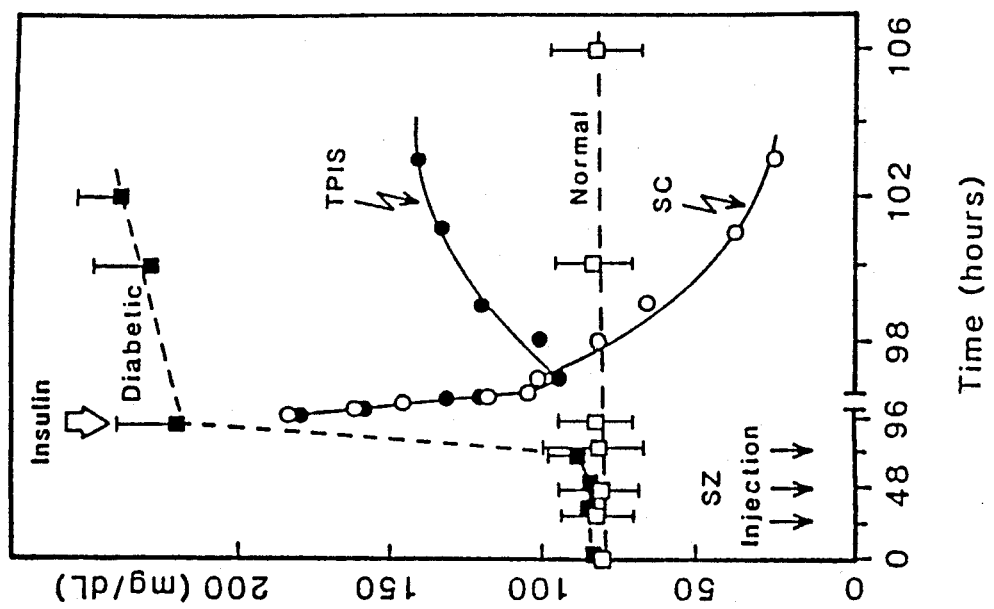
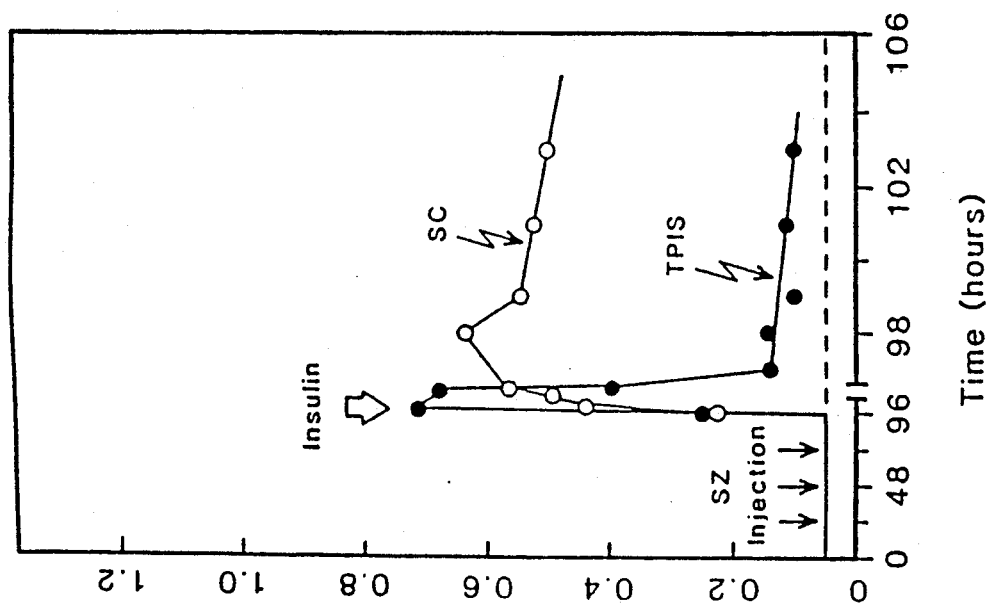
FIG. 24B
FIG. 24A

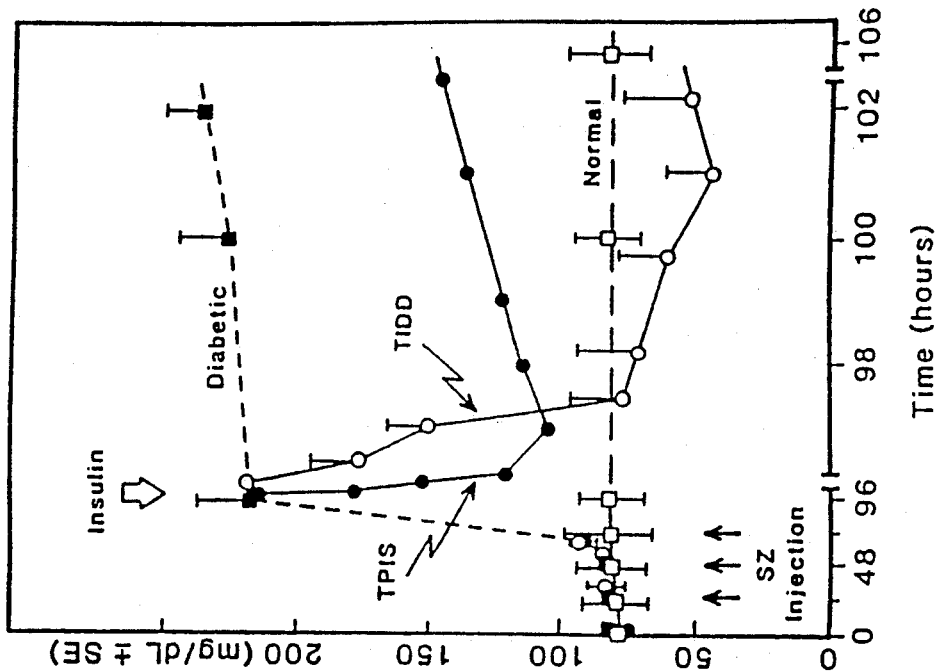
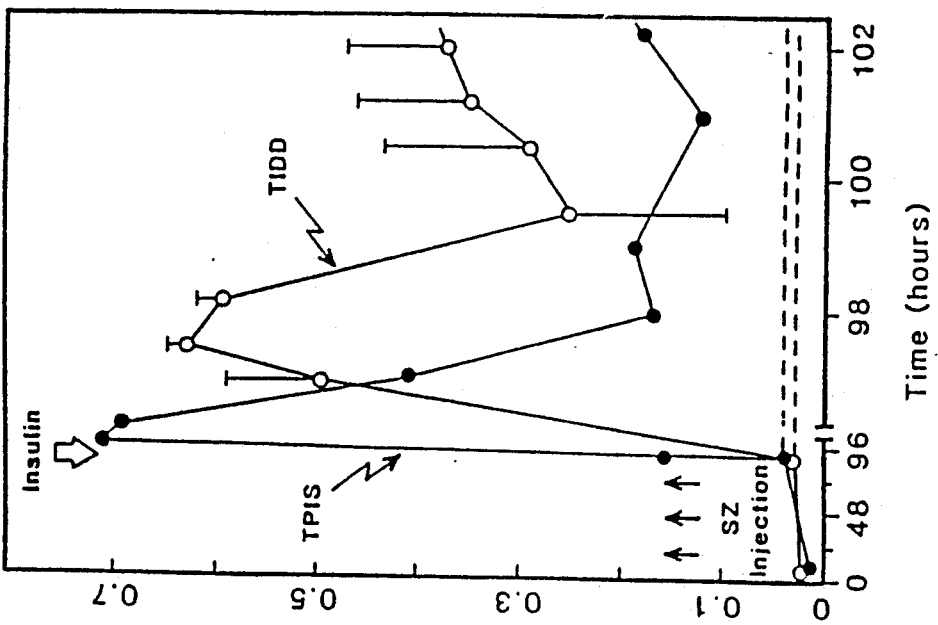
FIG. 25B
FIG. 25A

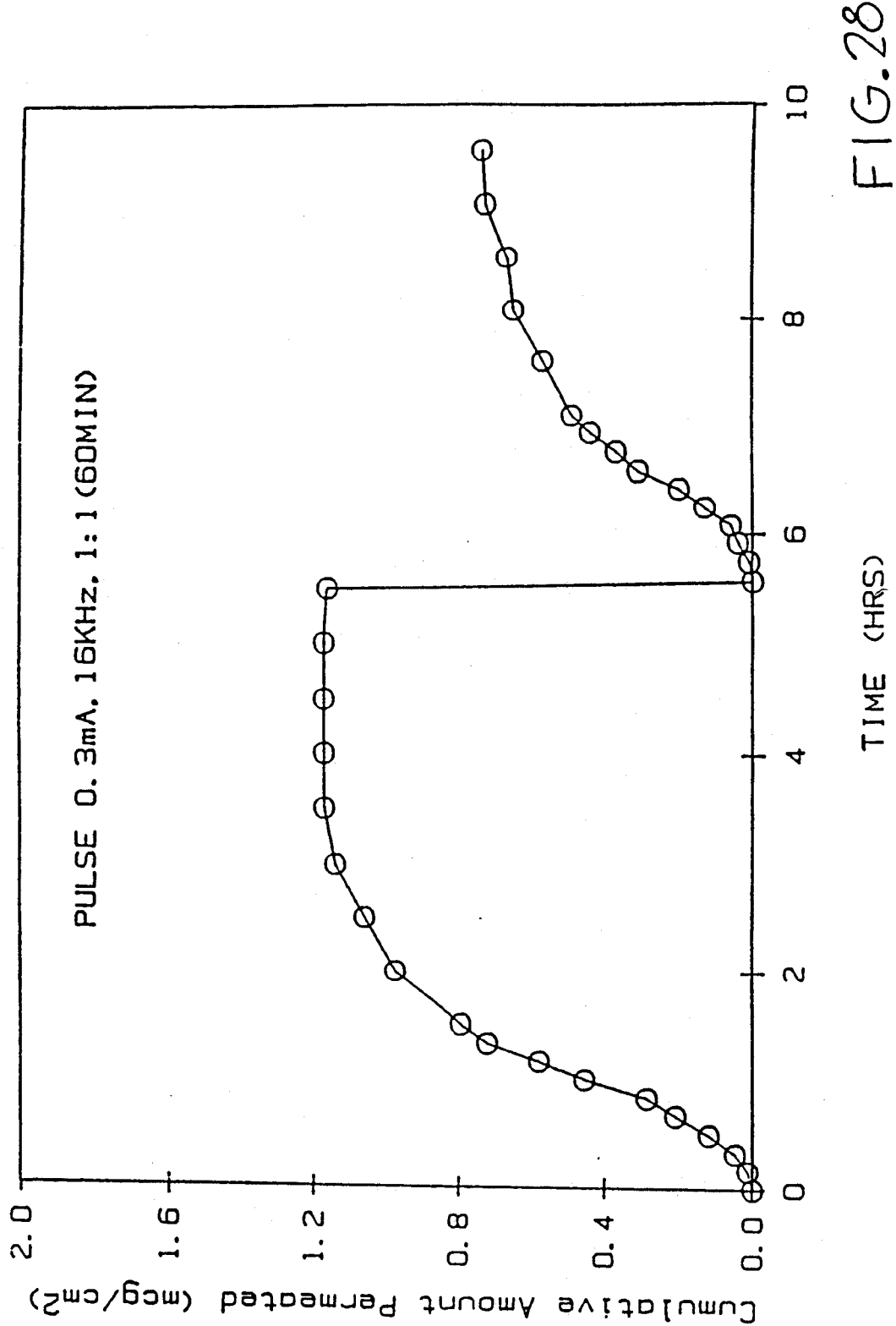

IONTOTHERAPEUTIC DEVICE AND PROCESS AND IONTOTHERAPEUTIC UNIT DOSE

CROSS-REFERENCE TO RELATED APPLICATION

This application is a continuation-in-part of U.S. application serial No. 890,702 filed July 25, 1986.

TECHNICAL FIELD

This invention relates to development of an iontotherapeutic device for regulated transdermal systemic administration of ionizable pharmaceuticals (including ionizable biopharmaceuticals).

It also provides an iontotherapeutic process for transdermal administration of ionizable pharmaceuticals, particularly those which are otherwise transdermally absorbed to a small degree or not at all. The invention also relates to a polymeric unit dose in which an ionized pharmaceutical is dispersed. The unit dose is adapted to be assembled as a part of either the anode or the cathode, depending upon whether the ionized pharmaceutical is cationic or anionic, so that the ionized pharmaceutical will be delivered transdermally and then be absorbed systemically when the iontotherapeutic device is in operation.

BACKGROUND ART

Many pharmaceuticals are required to be administered to patients by injection. A notable example is insulin, which cannot be administered orally to be effective in lowering the elevated blood sugar levels, which are too high in diabetics (i.e., >126 mg/dL). Other pharmaceuticals may be administered orally, but in some cases, there is inefficient absorption into the bloodstream to permit the pharmaceuticals to achieve their intended therapy. Also, with regard to oral administration, many orally administered pharmaceuticals undergo a high degree of destruction by the hepato-gastrointestinal first-pass metabolism. Often the metabolites of the first-pass metabolism cause unwanted biological activity or toxicity. In oral administration, there are variables which cause undesirable variations in the extent of gastrointestinal absorption from subject to subject, especially in the case of some pharmaceuticals; and there are also associated problems of uneven blood levels resulting from an initial large absorption with attendant undesirable side effects or toxicities, and subsequent blood levels which are less than therapeutically optimal.

Recently there has been an increasing interest in transdermal delivery. However, transdermal absorption of a number of pharmaceuticals, particularly the macromolecular drugs such as insulin and cationic drugs like propranolol HCl, has not been satisfactorily developed for adequate therapy, since they have not been absorbed transdermally to any significant degree.

The hazard and discomfort of administration of pharmaceuticals by injection, especially if therapy is required on a frequent basis, such as the subcutaneous injection of insulin for diabetes therapy, which is required daily, are universally known. There has long been a desire to avoid the necessity of therapy by injection.

Investigations have been carried out to explore the possibility of delivering certain therapeutic agents topically by use of a direct current (DC) iontophoresis. For example, it has been found that fluoride ions can be assimilated into the structure of a tooth with the aid of DC iontophoresis. Also, localized "sweating" has been caused by delivering to the skin a sweat-inducing compound, such as pilocarpine, using a direct current. The induced sweat is then assayed using an electrode to determine its chloride ion concentration for diagnosis purposes. A low chloride content in the sweat indicates that a patient may be suffering from cystic fibrosis. Application of a DC iontophoresis can be uncomfortable particularly when the level of applied current is at a high level, in the case of certain pharmaceuticals, in order to achieve a systemic therapeutic level.

It is highly desired to provide improved iontotherapeutic devices and processes and unit dose forms for use therein and to provide further thereby therapeutic levels of systemically-effective pharmaceuticals efficiently with a physiologically-acceptable low electric current.

SUMMARY OF THE INVENTION

A process has been found for administering transdermally a systemically effective amount of an ionizable pharmaceutical in sterile aqueous solution using an iontotherapeutic device such as provided by this invention. The ionized pharmaceutical solution can be contained in a unit dose form such as disposable polymeric matrix unit dose form in which a dosage amount of an ionized pharmaceutical solution (pH desirably at least about 1.0, 1.5 or about 2 pH units above or below the pKa or isoelectric pH of the ionizable pharmaceutical) is intermixed with a polymer which is characterized by being compatible with the pharmaceutical as well as the skin, hydrophilic, and capable of releasing the pharmaceutical for iontotherapeutic transdermal absorption. The unit dose form can also comprise a sterile solution of the ionized pharmaceutical contained within a closed reservoir unit dose form having a drug-releasing microporous membrane surface. The unit dose forms are assembled with a pharmaceutical reservoir electrode and are further adapted to permit the dissolved, ionized pharmaceutical to be delivered iontophoretically to the skin of the subject treated and to provide iontotherapeutic transdermal absorption of a systemically effective amount of the pharmaceutical. The unit dose forms are maintained covered to retain sterility until the desired time of iontotherapeutic administration. A pharmaceutical reservoir electrode which will receive such a unit dose form is used as a part of the iontotherapeutic device, such as provided by this invention, which is used to carry out the iontotherapeutic delivery and transdermal absorption of the ionized pharmaceutical. The pharmaceutical reservoir electrode is either a cathode or an anode depending upon whether the pharmaceutical is in anionic or cationic form, respectively. The iontotherapeutic device provides, in the process, an iontotherapeutically effective and physiologically acceptable pulse current with a specific waveform having an amplitude up to about 10 mA based on a reservoir electrode skin-contacting area of about 5 $cm^2$ and an effective frequency of at least about 10 Hz up to about 50 KHz until the subject treated has received a pharmacologically-effective systemic dosage of the ionized pharmaceutical.

Also, provided by this invention is a unit dose form adapted for use in a pharmaceutical reservoir electrode and to be used in electrical contact with intact skin of a subject to be treated with the pharmaceutical. The unit dose can have a polymeric matrix in which the pharmaceutical is ionized and in solution and also contained and distributed within the polymeric matrix. The polymer of the matrix is compatible with the pharmaceutical as well as the skin, permits release of the pharmaceutical from the unit dose form, so it can be iontotherapeutically delivered for transdermal absorption. The polymer used is hydrophilic. The pharmaceutical in the unit dose form can be selected from pharmaceuticals which ordinarily are not transdermally absorbed through intact skin in an effective dosage amount, such pharmaceuticals including but not limited to insulins, vasopressin, heparin, growth hormones, glucagon, oxytocin, and other macromolecular drugs as well as a number of others which can be provided in ionized form. A number of compounds which are naturally-occurring in humans, and which often are peptide in nature, are also included within this pharmaceutical group, many of which can be produced identically or as a related compound using DNA recombinant or other biological techniques.

Also provided by the invention is a novel iontotherapeutic device capable of transdermally administering a systemically effective amount of an ionized pharmaceutical. The device comprises:

(1) A DC power supply capable of providing a therapeutically effective and physiologically acceptable pulse current in the range of up to about 10 mA;

(2) A periodic waveform generator having integrated circuitry capable of providing an iontotherapeutically effective periodic current waveform in either the square, triangular, sinusoidal, trapezoidal, or other acceptable geometric shape or any combinations; an on/off ratio of about 1/50 to about 10/1 desirably about 1/10 to about 8/1; and a physiologically acceptable repetition frequency in a range of at least about 10Hz, which range can vary up to about 5 KHz and beyond to about 50 KHz;

(3) an output circuit which provides a passage of a selected waveform, monitors dose current and adjusts dose current to maintain the current within a predetermined iontotherapeutically effective range, and delivers the current to a pharmaceutical reservoir electrode for transdermal iontotherapeutic administration of said pharmaceutical to the intact skin treated;

(4) a pharmaceutical reservoir electrode which is selected to be either the cathode or the anode depending, respectively, whether the ionized pharmaceutical is in anionic or cationic; said electrode comprising a receptacle base adapted to receive a sterile aqueous solution of an ionized pharmaceutical such as a pharmaceutical-containing unit dose form in which the pharmaceutical is in aqueous solution and which is adapted to be in electrical contact with intact skin to be treated when said device is in iontotherapeutic operation, said pharmaceutical solution having an iontotherapeutically effective pH higher or lower than the isoelectric point or the pKa value of said pharmaceutical to provide said pharmaceutical in ionized form; said electrode base having a terminal means to receive said DC current at a selected periodic waveform for transmission through said ionized unit dose of pharmaceutical solution; and (5) a second electrode adapted to be in electrical contact with the intact skin to be treated and forming with said pharmaceutical reservoir electrode a combination of anode and cathode electrodes.

BRIEF DESCRIPTION OF THE DRAWINGS

FIG. 23A is a graph showing lowering of blood sugar level (B.G.L.) of hairless rats using transdermal periodic iontotherapeutic system on Day 1 using insulin solution at pH 3.68.

FIG. 23B is a graph showing further lowering of the blood sugar levels of the same rats on Day 3 using transdermal periodic iontotherapeutic system without further administration of insulin, indicating that the insulin delivered transdermally on Day 1 is stored in the skin tissues and can be activated to become available for absorption into systemic circulation on Day 3 by TPIS.

FIG. 24A is a pair of comparative graphs showing plasma immunoreactive insulin levels in diabetic rabbits after administration of insulin solution (pH 7.1) using transdermal periodic iontotherapeutic system (TPIS) compared with corresponding levels in diabetic rabbits using subcutaneous administration (SC). "SZ injection" indicates injections to render rabbits diabetic.

FIG. 24B is a pair of comparative graphs corresponding to those of FIG. 24A showing the respective reduction of blood glucose levels (B.G.L.). The data show that blood glucose levels can be controlled at a highly constant level so as not to fall substantially, if at all, below normal level by TPIS.

FIG. 25A is a pair of comparative graphs showing the increase in plasma insulin concentration after administration of insulin solution (pH 7.10) using transdermal periodic iontotherapeutic system (TPIS) compared to using transdermal ionotherapeutic system (TIDD) in which 4× current intensity and 2× administration times are used. TPIS administration shows more rapid attainment of increased plasma insulin concentrations.

FIG. 25B is a pair of comparative graphs corresponding to those of FIG. 25A showing the attained lowering of blood glucose levels (B.G.L.). The data show a near instantaneous reduction of blood glucose level from the hyperglycemic level in the diabetic controls using transdermal periodic iontotherapeutic sYstem (TPIS) whereas the reduction using transdermal iontotherapeutic system (TIDD) is lower than the normoglycemic level.

FIG. 28 is a graph showing enhancement of skin permeation of vasopressin using TPIS with a short skin permeation lag time. The graph also shows reversibility of skin permeation within 2 hours after ceasing TPIS treatment and again enhancement of skin permeation after reinstituting TPIS.

DETAILED DESCRIPTION OF THE INVENTION AND THE PREFERRED EMBODIMENTS

Figure 1:
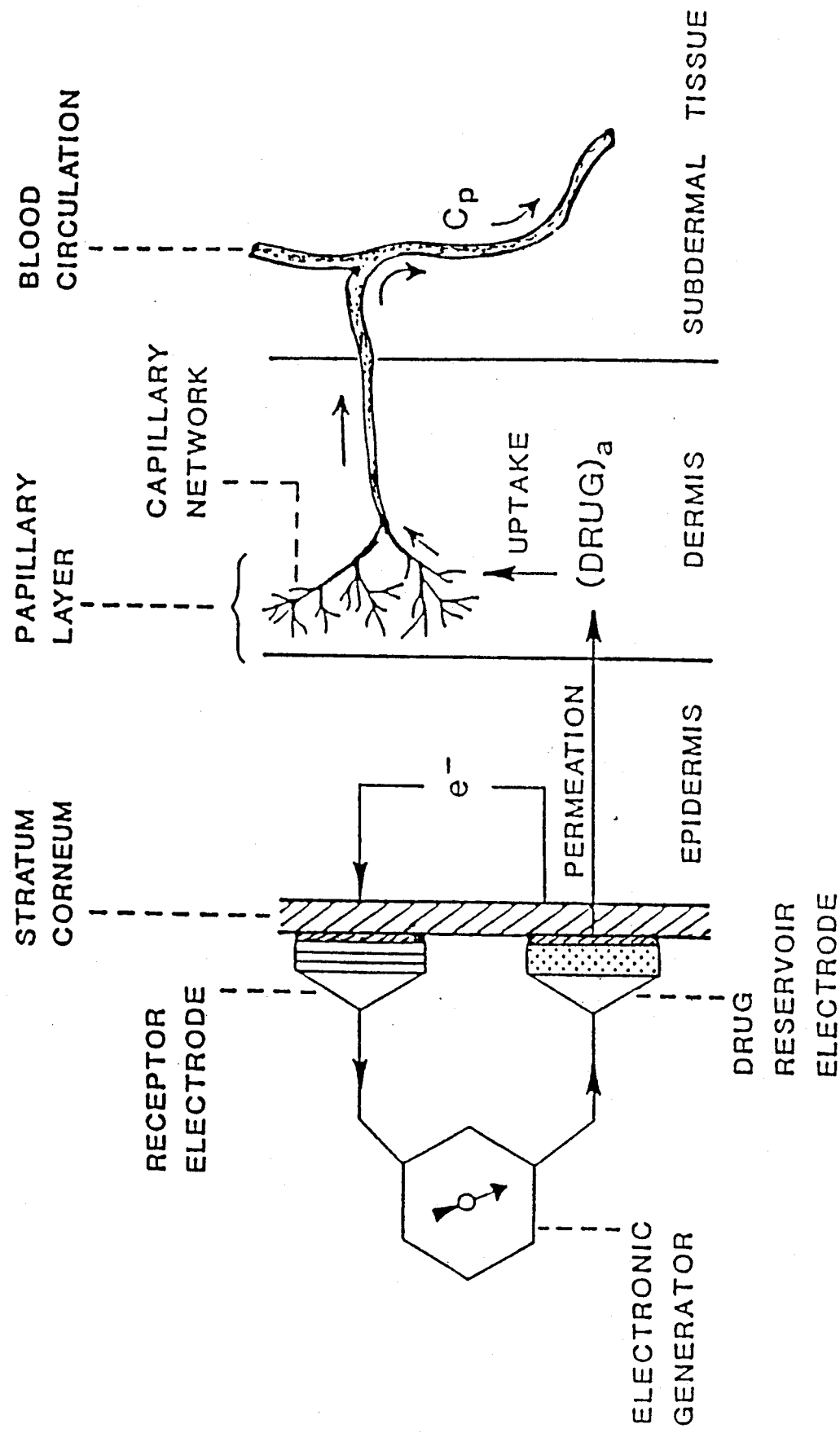
FIG. 1 is a diagram portraying a device of the invention in operation to effect iontotherapeutic transdermal absorption of an ionized pharmaceutical and its uptake into the bloodstream of the subject treated.

FIG. 1 is a diagram portraying a device of the invention in operation to deliver iontotherapeutically an ionized pharmaceutical and its uptake into the blood stream of the subject treated. The figure shows the iontotherapeutic device in electric contact with the skin.

It also shows the pharmaceutical reservoir electrode in contact with the skin as well as the other electrode, which is referred to as the receptor electrode. The electrodes are in contact with the uppermost skin barrier, called stratum corneum. The pharmaceutical is transmitted through the stratum corneum and flows into the dermo-epidermal layer. The stratum corneum is the principal absorption rate limiting barrier. The first portion of the dermis layer is referred to as the papillary layer, which contains a capillary network of the vascular system. The capillary network takes up the transdermally absorbed pharmaceutical and the uptaken pharmaceutical is shown to flow from the capillary network into the main portion of the vascular system.

Figure 2:
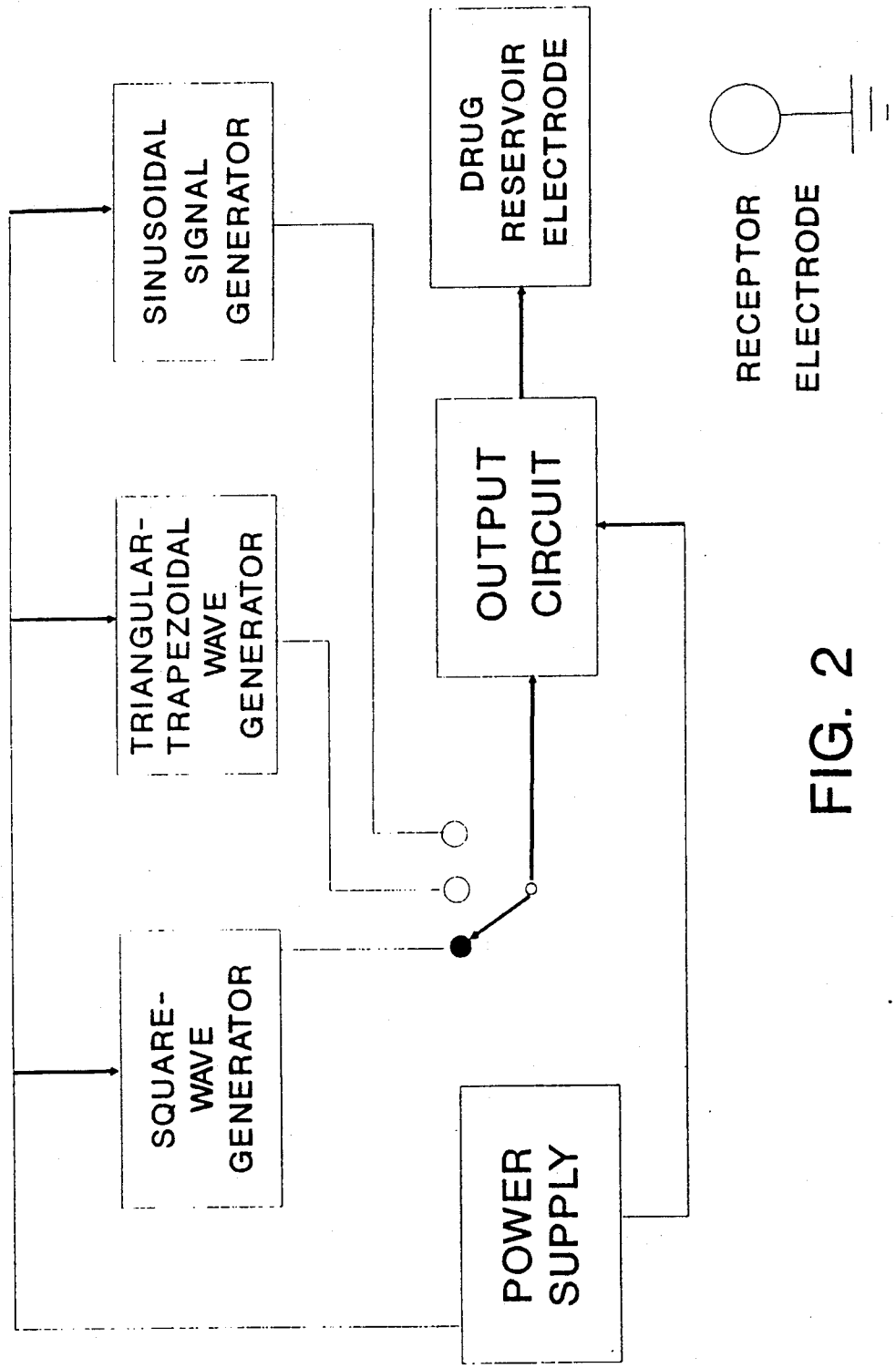
FIG. 2 is a block diagram of a transdermal periodic iontotherapeutic device coming within the invention.

FIG. 2 is a block diagram of a transdermal periodic iontotherapeutic device coming within the invention in which the power supply is derived either from the conversion of the alternate current (AC) from a 120 V-mains (or other available AC mains) into direct current or from a suitable battery. The power is turned on manually by a switch or automatically by a programmable timer. The device also consists of one or a combination of several electronic multifunction generators, a drug reservoir electrode and a receptor electrode. The multifunction generator is assembled with a power supply, to deliver direct current with periodic waveform of either square, triangular, trapezoidal or sinusodial shape, to an output circuit. The desired iontotherapeutically-effective waveform can be selected manually or preprogrammed through a switch ($K_1$), and the frequency of the output waveform can be adjusted in the range of 10 Hz–50 KHz. The output circuit then provides a physiologically acceptable current, ranging up to 10 mA, to the pharmaceutical reservoir electrode which contains the ionized pharmaceutical to be delivered transdermally, and a receptor electrode in series. When desired, the device can be operated to deliver either DC current alone (periodically or continuously), or in combination with a periodic waveform.

Figure 3:
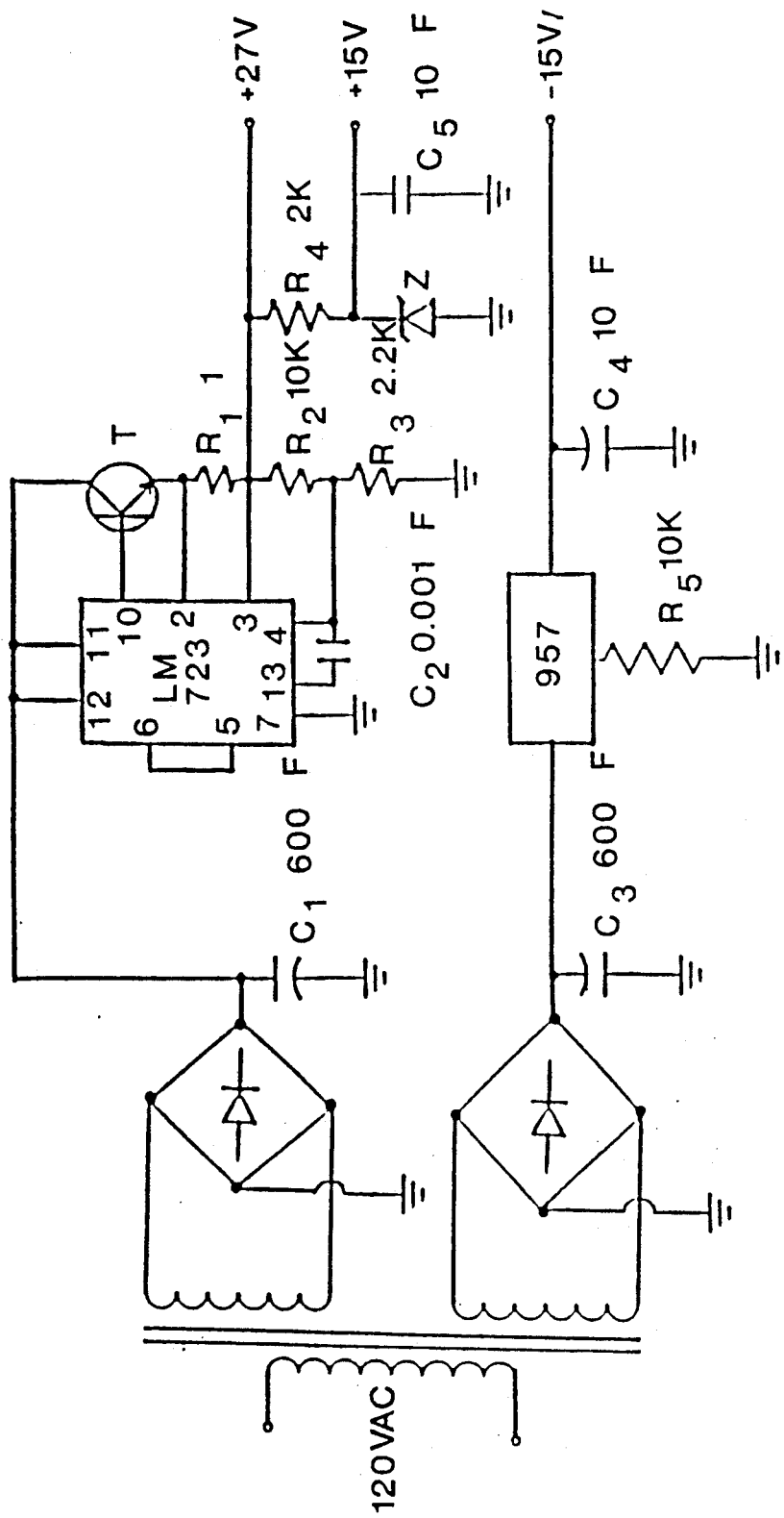
FIG. 3 is a detailed circuit diagram for the Power Supply shown in FIG. 2.

FIG. 3 is a detailed circuit diagram for the power supply shown in FIG. 2. It converts the AC current from a 120 V-mains to a DC current at ±15 V and +27 V through 2 voltage regulators, 957 and LM 723, respectively. C's and R's designate capacitors and resistors, respectively. In case the power supply is derived from 120 V-alternate current, it is stepped down by a step-down transformer and then full-wave rectified by a diode bridge rectifier. The transistor (T) boosts the output current of LM723 to the required level. The +27 V output branches, through the Zener diode (Z) in the branch, to provide a +15 V output voltage. Capacitors of 600 F and 10 F serve to smooth the output voltage. The other resistors and capacitor are required in the operation of the voltage regulation elements.

Figure 4:
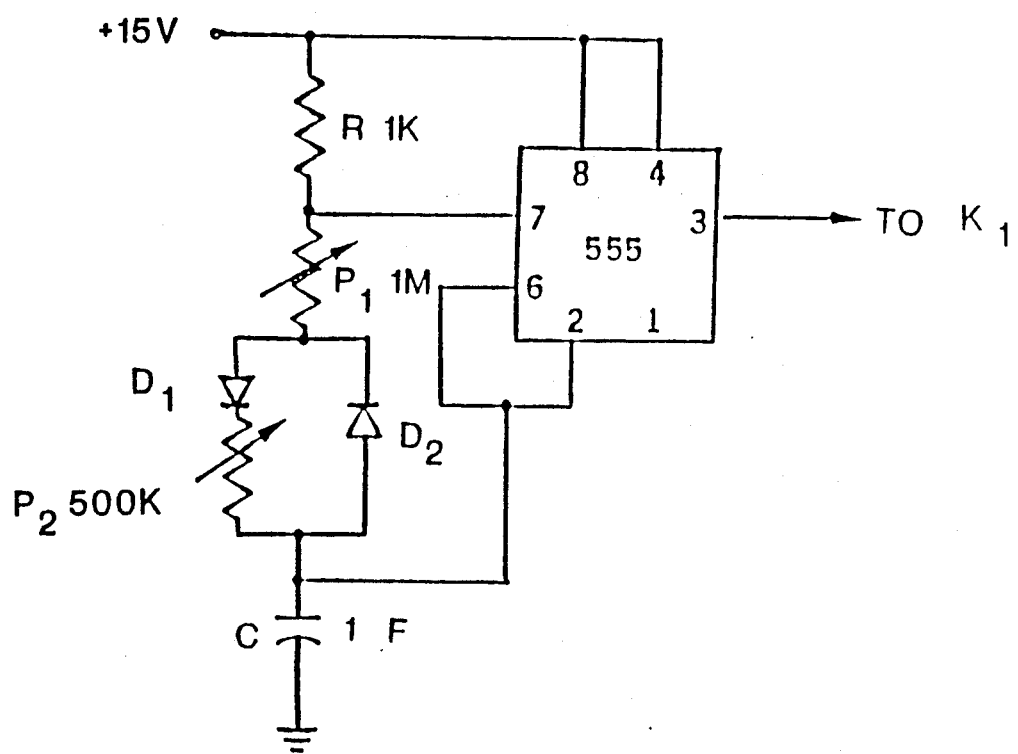
FIG. 4 is a detailed circuit diagram for the Square-Wave Generator shown in FIG. 2.

FIG. 4 is a detailed circuit diagram for the square-wave generator shown in FIG. 2. It employs a microchip 555 timer. The frequency (F) of the square wave is:

$$F = \frac{1}{t_1 + t_2}$$
$$t_1 = 0.693(P_1 + P_2)C$$
$$t_2 = 0.693\, P_1\, C$$

where P's are potentiometers, C is a capacitor, and D's are diodes. During the operation, the capacitor C is charged through the potentiometer $P_1$ and $P_2$ and the diode D for $t_1$ seconds and discharged through potentiometer $P_1$ and diode $D_2$ for $t_2$ seconds.

Figure 5:
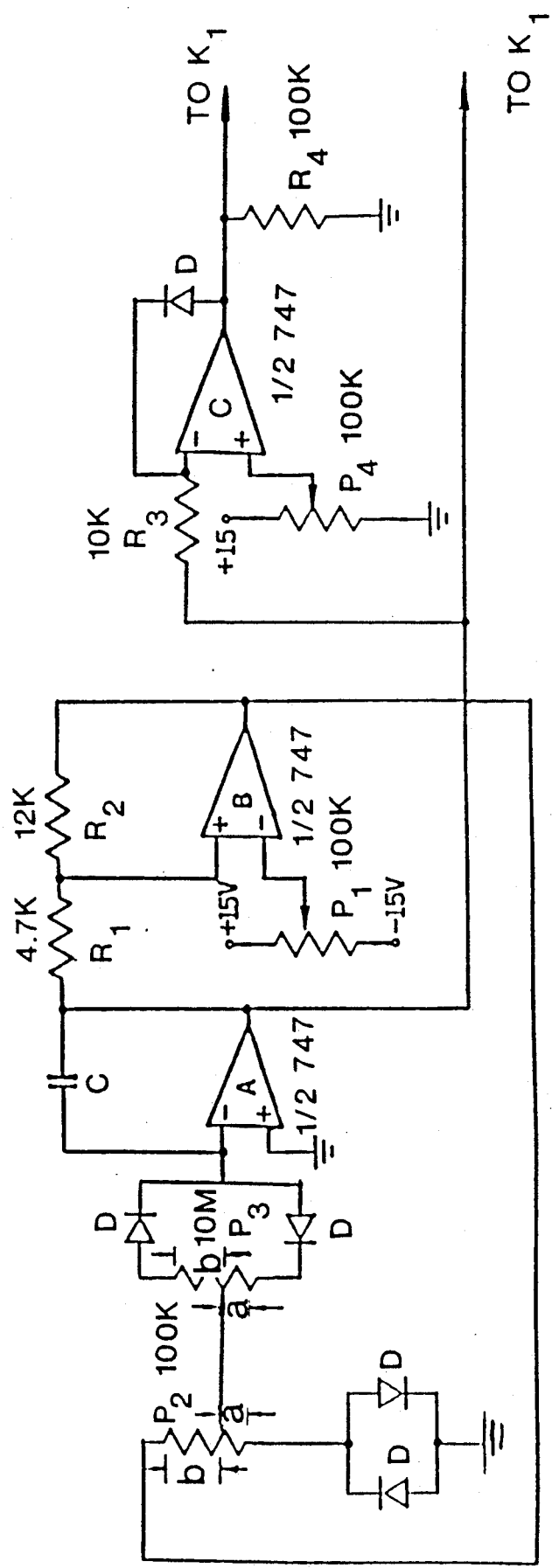
FIG. 5 is a detailed circuit diagram for the Trapezoidal-Triangular Wave Generator shown in FIG. 2.

FIG. 5 is a detailed circuit diagram for the triangular-trapezoidal waveform generator shown in FIG. 2. It consists of an integrator (A) and a regenerative comparator (B) connected in a positive feedback loop. Precise triangular waves are formed by integration of the square wave which is feed back from the output of the comparator to the input of the integrator. The frequency (F) of the triangular wave is:

$$F = \frac{1}{t_1 + t_2} \quad t_1 = \frac{(V_o^+ - V_o^-)}{R_2} R_1 / \frac{V_o^-}{C(P_{2a} - P_3b)}$$
$$t_2 = \frac{(V_o^+ - V_o^-)}{R_2} R_1 / \frac{-V_o^-}{C(P_{2b} - P_{3a})}$$

where $V_o^+$ and $V_o^-$ are the higher and lower trip points of the comparator, respectively. Resistors $R_1$ and $R_2$ control the comparator trip points. Capacitor C is the integration capacitor. Potentiometer $P_1$ provides adjustment of the triangular wave offset. Potentiometers $P_2$ and $P_3$ adjust frequency and symmetry, respectively.

The third op-amp circuit (C) acts as a damper. It produces a trapezoidal wave with the same frequency as the triangular wave. Potentiometer $P_4$ sets the clamping level.

Figure 6:
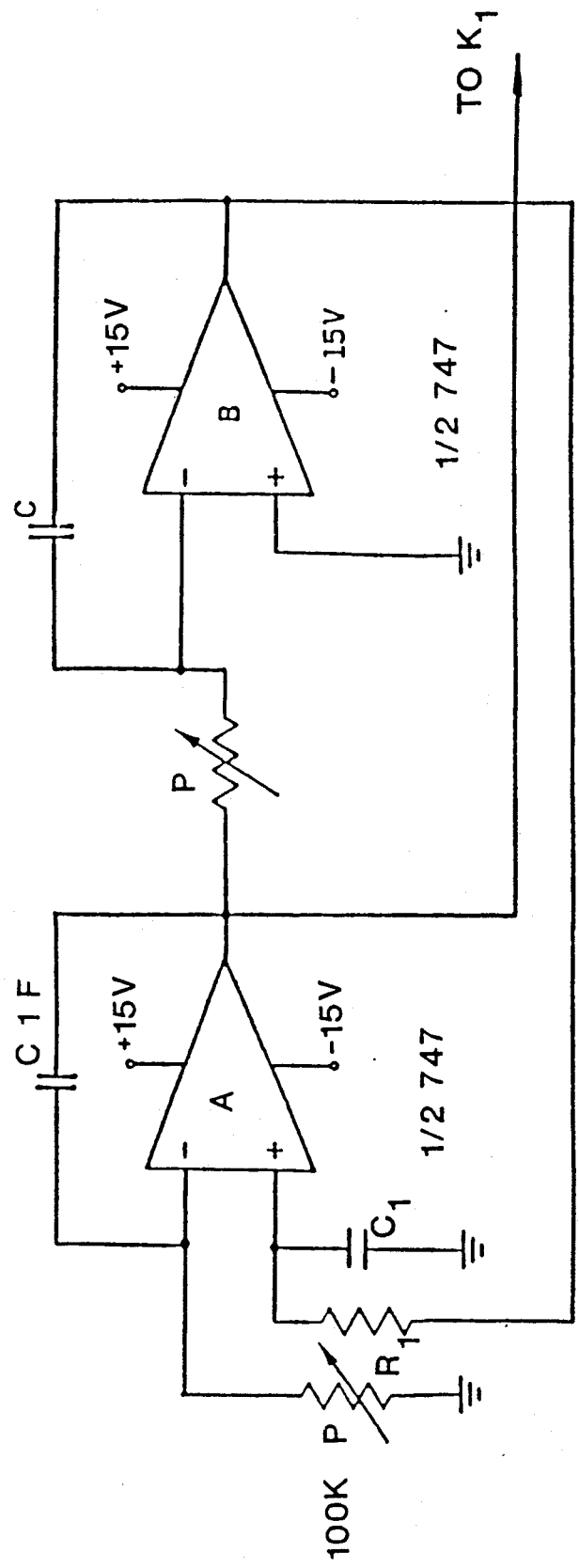
FIG. 6 is a detailed circuit diagram for the Sinusoidal Signal Generator shown in FIG. 2.

FIG. 6 is a detailed circuit diagram for the sinusoidal signal generator shown in FIG. 2. The circuit of the generator uses two amplifiers: one (A) acts as a non-inverting integrator, and the other (B) acts as an inverting integrator. They are connected in cascade to form a feedback loop. The frequency (F) of the sinusoidal signal is determined by:

$$F = \frac{1}{2\, CP}$$

C's and P's are integration capacitors and the variable resistors, respectively. Resistor $R_1$ is a feedback resistor. Capacitor $C_1$ is used to prevent high-frequency oscillations.

Figure 7:
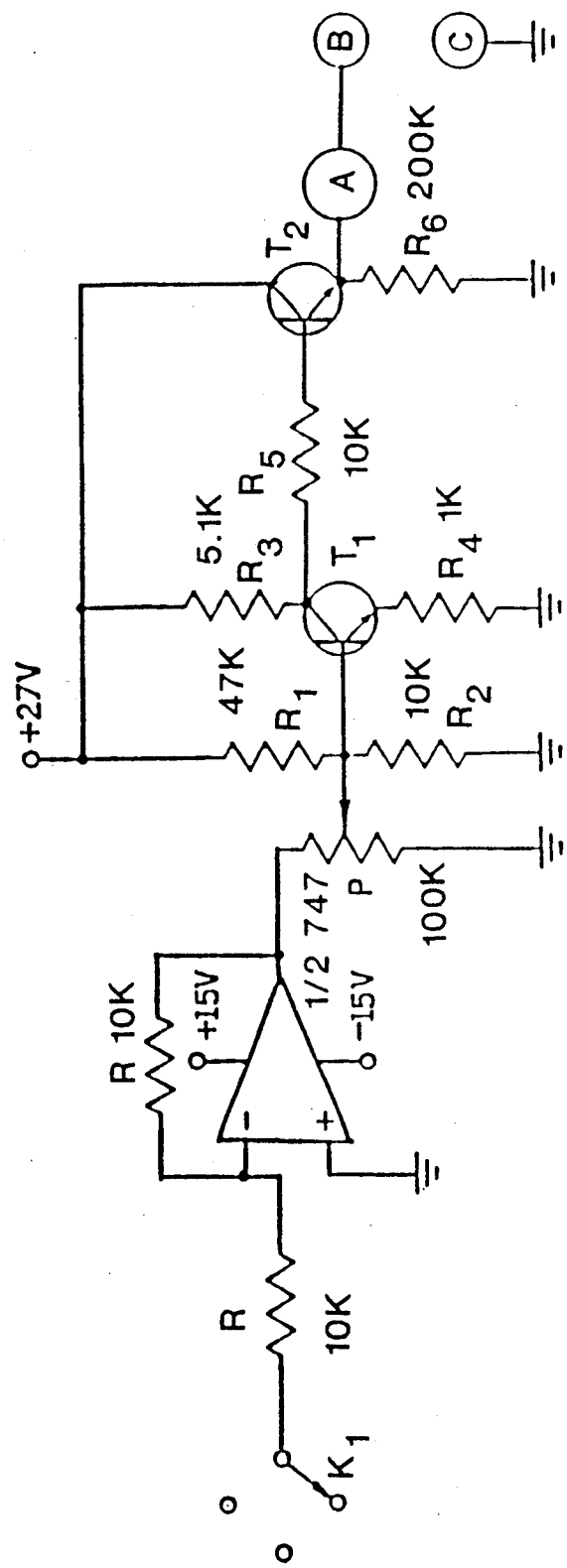
FIG. 7 is a detailed circuit diagram for the Output Circuit shown in FIG. 2.

FIG. 7 is a detailed circuit diagram for the Output Circuit shown in FIG. 2. The desired waveform is selected manually or automatically from the 3 generators through a switch ($K_1$) and sent to the inverting amplifier, from which the signal then goes to the output stage of two transistors. The output current (dose current) is adjusted by a potentiometer (P), as monitored by a current meter (A), and is delivered to the drug reservoir electrode (B).

Figure 8:
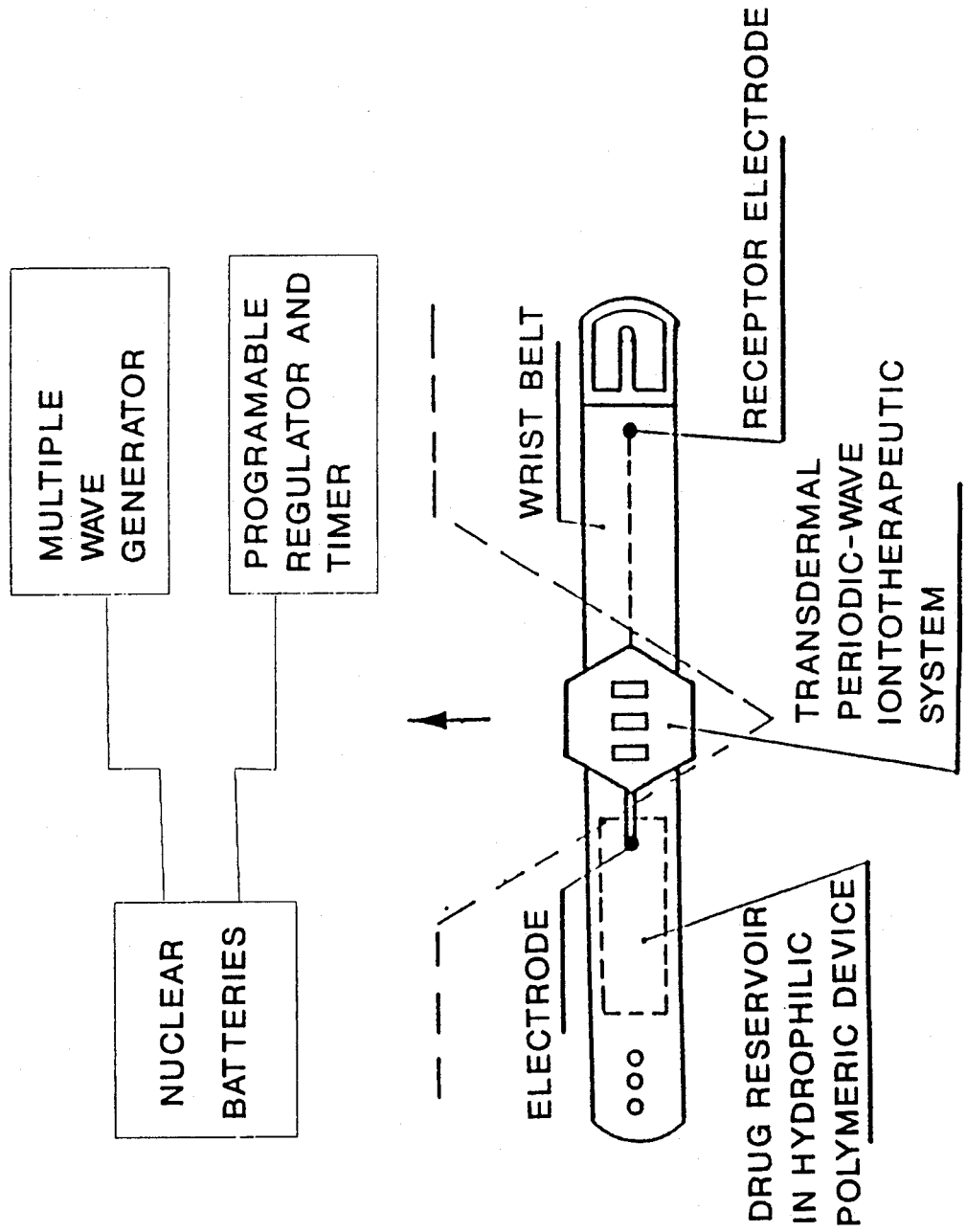
FIG. 8 is a block diagram of a wristwatch-type miniaturized periodic iontotherapeutic device coming within the invention, in which the drug reservoir electrode is positioned away from the main portion of iontotherapeutic device.

FIG. 8 is a diagram illustrating the wristwatch-type miniaturized transdermal periodic iontotherapeutic system with multifunction programmability. It is designed to have one or more nuclear batteries and two pieces of microchips: One is for the purpose of generating different waveforms, as outlined in FIGS. 4-6, and the other is for the purpose of controlling and to display the output current. The nuclear batteries provide the energy needed for long-term operation. For instance, the programmability may include selection of DC alone or in combination with a periodic waveform, a dose current for a particularly designated time period. In certain applications, it may be advantageous in operating the devices of this invention to have the periodic current waveform remaining at some constant DC level during the off cycle. In this design of iontotherapeutic device, the drug reservoir electrode is positioned outside the device.

Figure 9A:
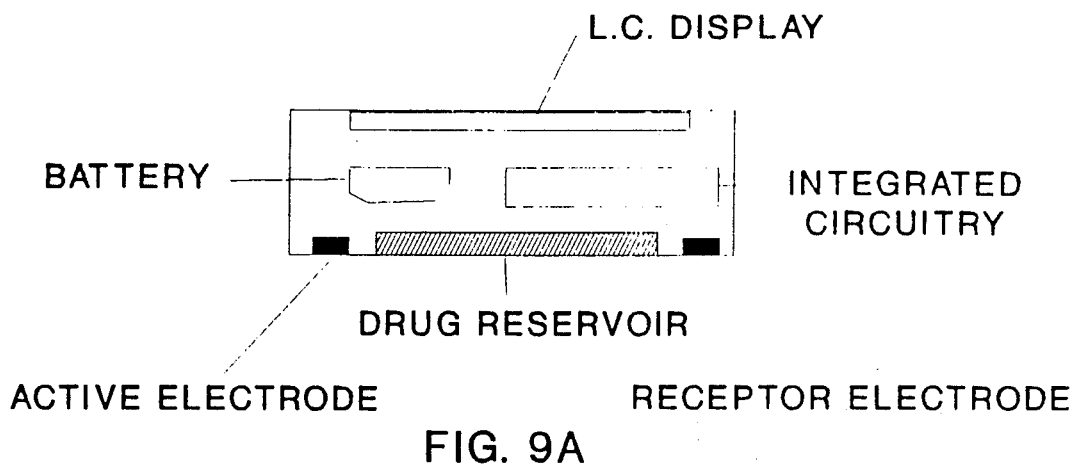
FIG. 9 is a diagram illustrating the wristwatch-type miniaturized transdermal periodic iontotherapeutic system with the drug reservoir electrode positioned directly in the lower portion of the iontotherapeutic device and with multifunctional programmability.
Figure 9B:
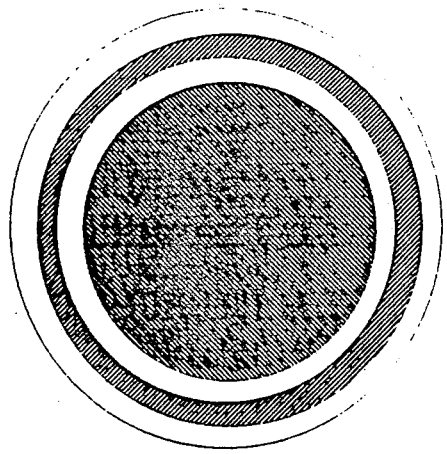

FIG. 9 shows an embodiment of another design of iontotherapeutic device coming within the invention. It shows two views of the device. The first view is a cross-sectional view showing the integrated circuitry, L.C. display, battery, drug reservoir electrode positioned directly in the lower central portion of the base and the receptor electrode encircling the drug reservoir electrode. The next view shows the bottom view of the device. In the center portion of the bottom view is shown the circular drug reservoir portion of the drug reservoir electrode. The drug or pharmaceutical dissolved in an aqueous solution is homogeneously dispersed in a polymer matrix unit dose as described herein. The pharmaceutical solution can also be contained in a reservoir-type unit dose having a microporous surface adapted to permit the drug to be transmitted. Next, there is shown the receptor electrode, as a circular ring positioned in spaced relationship from the drug reservoir electrode. At the top of the cross-sectional view is shown a liquid crystal display. It can display a number of functions, including whether or not the device is in operations the type of periodic current and waveform being used and other pertinent information of the transdermal periodic iontotherapeutic drug delivery. The battery employed as the power source for this invention can be a lithium or other nuclear battery having a voltage, for example, of from 6 to 12 volts.

Figure 10:
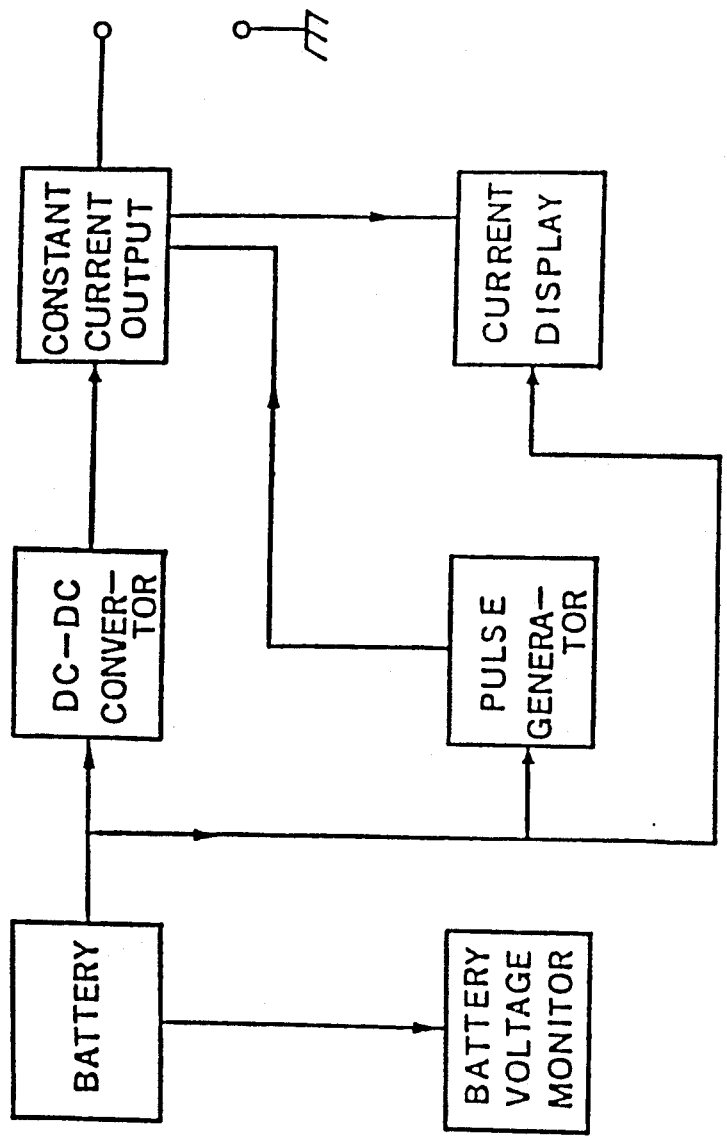
FIG. 10 is a block diagram of a portable transdermal periodic iontotherapeutic device coming within the invention.

FIG. 10 is a block diagram of a portable transdermal periodic iontotherapeutic device coming within the invention in which the power supply is derived from a battery source such as one or more 9 V batteries. The power is turned on manually by a switch. The device can be equipped so that it can be turned on automatically by a programmable timer. The device also consists of one or a combination of several electronic multifunction generators, a drug reservoir electrode and a receptor electrode. The multifunction generator can provide periodic waveform of either square, triangular, trapezoidal or sinusodial shape, to an output circuit. The desired iontotherapeutically effective waveform can be selected manually and the frequency of the output waveform can be adjusted to a physiologically acceptable frequency of at least 10 Hz and up to about 50 KHz. The output circuit then provides a physiologically acceptable current, ranging up to 10 mA, to the pharmaceutical reservoir electrode, which contains the solution of the ionized pharmaceutical to be delivered transdermally, and a receptor electrode in series. When desired, the device can be operated to deliver either DC current alone (periodically or continuously), or in combination with a periodic waveform.

Figure 11A:
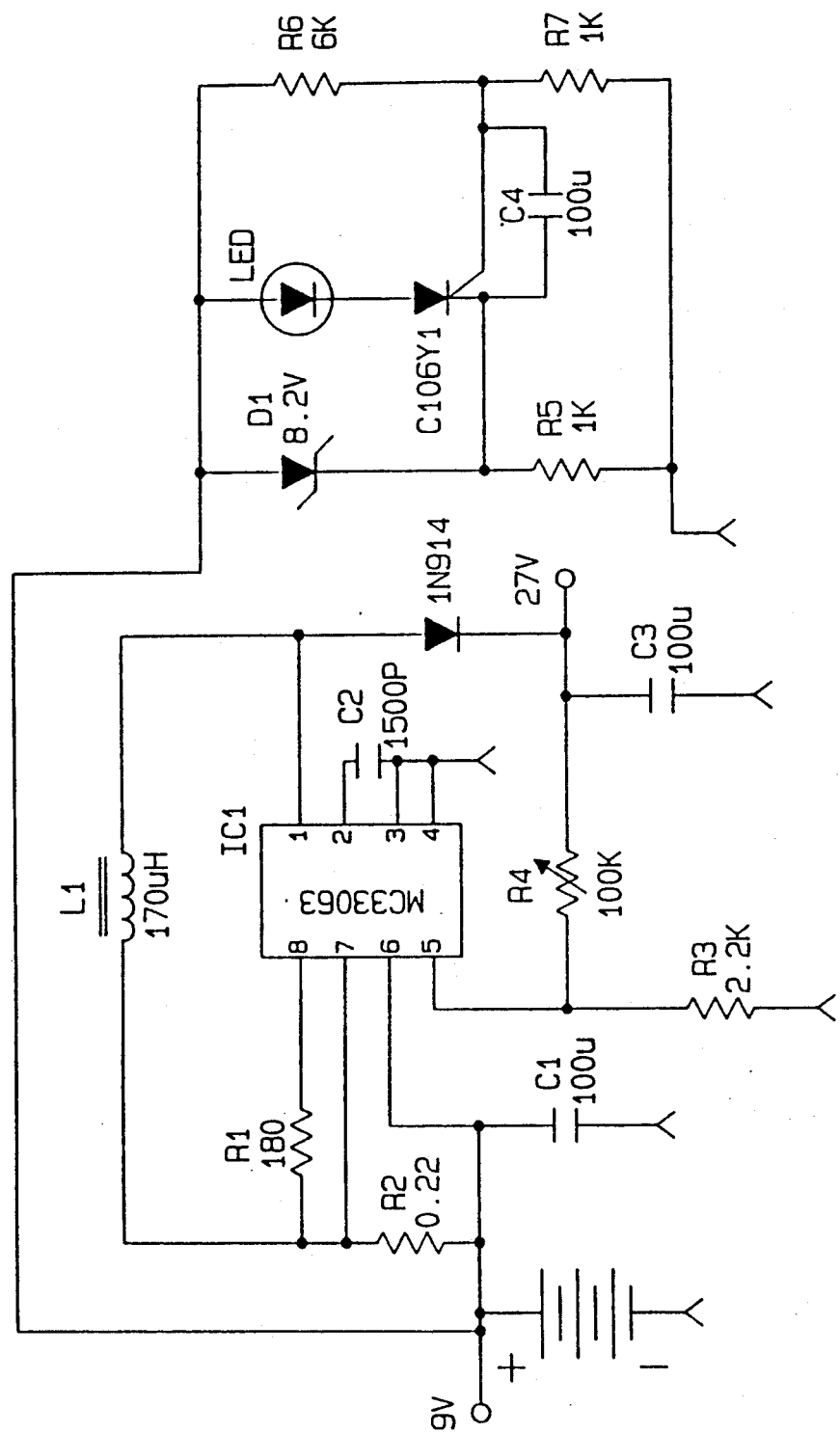
FIG. 11 is a detailed circuit diagram of the device shown in FIG. 10.

FIG. 11 is a detailed circuit diagram for the portable transdermal periodic iontotherapeutic device shown in the block diagram of FIG. 10. Referring to FIG. 11, the following is a description of the circuits and their functioning:

The DC-to-DC-converter-and-battery-voltage-monitor $IC_1$, $R_1$–$R_4$, $C_1$–$C_3$, L1 and diode IN914 consist of a DC-to-DC converter which is incorporated in step-up application. The output voltage is elevated from 9 V battery to 27 V with the proper adjustment of $R_4$. The output voltage of the battery is monitored by a battery voltage monitor which includes a zener diode $D_1$, $R_5$–$R_7$, $C_4$ and $C_{106}Y1$. When output of 9-V battery drops below minimum acceptable volume of 8.3 V, LED lights to indicate the need for recharging.

Pulse generator and constant current output stage.

$IC_2$, $D_2$–$D_5$, $T_1$, $C_5$, $C_6$ and $R_8$ are components of a triangle-wave generator. In this circuit, the charge and discharge currents for $C_6$ come through the diode bridge formed by $D_2$–$D_5$. Bridge $D_2$–$D_5$ consists of four general purpose switching diodes with low-leakage characteristics, that serve to steer current in the proper direction through the current source made up of $T_1$ and $R_8$.

The pin 3 of $IC_2$ serves as a source of current for the timing network, and its state of high or low determines the direction of current flow into or out of $C_6$ for charge or discharge. Since both charge and discharge currents flow through the same current regulator circuit, the currents are equal and thus times of charge and discharge are equal. As a result, triangular waves are formed across $C_6$.

The circuit covers the frequency range of about 20 Hz to 30 KHz. The adjustment of the frequency is done with $R_8$. The frequency of the triangle waves can be expressed as $$f = \frac{1}{5R_8C_6}$$

The output of the triangle-wave generator is sent to the pin 3 of $IC_3$ which serves as a comparator. The voltage comparison is made between pin 2 and pin 3 of $IC_3$ The square waves are formed at pin 7 of $IC_3$ with a duty cycle which is determined by the voltage of the voltage divider composed of $R_{10}$–$R_{12}$ The higher the voltage applied to pin 2 is, the shorter the "on" time of the square waves, and vice versa. The duty cycle of the square waves covers the range of 1/10 to 10/1. The square waves are amplified by $T_2$–$T_4$ and sent to pin 11 of $IC_4$.

In constant current output stage, $IC_{723}$ is employed to serve as a current regulator. $IC_{723}$ is originally designed to be a voltage regulator with an output current limit resistor R across pin 10 and pin 3. The maximum output current is set as 0.6/R. This feature is adapted to form a current regulator. As soon as the condition $(V_{out}R_L) > I_s$ is satisfied (where $V_{out}$ is the output voltage, $R_L$, load resistance, and Is, output current preset), the output current will be kept at the preset level.

$R_{21}$ is the minimum current limit resistor. $R_{22}$ is used to preset the desired output current. $C_7$ and $R_{20}$ are used to eliminate high frequency noise.

Output current monitor

Intersil 7106 interfaced with a liquid crystal display is the heart of the current monitor. $R_{23}$ is a shunt resistor. $C_8$ and $R_{24}$ consist of a RC oscillator which runs at about 48 KHz and is divided by four prior to being used as the system clock. $C_{10}$ and $R_{27}$ serve as an input filter. $C_{11}$, $C_{12}$ and $R_{28}$ determine the display sensitivity. $C_9$ is for auto-zero function.

The power is turned on manually by a switch or automatically by a programmable timer. The device also consists of one or a combination of several electronic multifunction generators, a drug reservoir electrode and a receptor electrode. The multifunction generator is assembled with a power supply, to deliver direct current with periodic waveform of either square, triangular, trapezoidal or sinusodial shape, to an output circuit. The desired iontotherapeutically effective waveform can be selected manually or preprogrammed through a switch ($K_1$), and the frequency of the output waveform can be adjusted in the range of 10 Hz-50 KHz. The output circuit then provides a physiologically acceptable current, ranging up to 10 mA, to the pharmaceutical reservoir electrode, which contains the pharmaceutical formulation to be delivered transdermally, and a receptor electrode in series. When desired, the device can be operated to deliver either DC current alone (periodically or continuously), or in combination with a periodic waveform.

Figure 12:
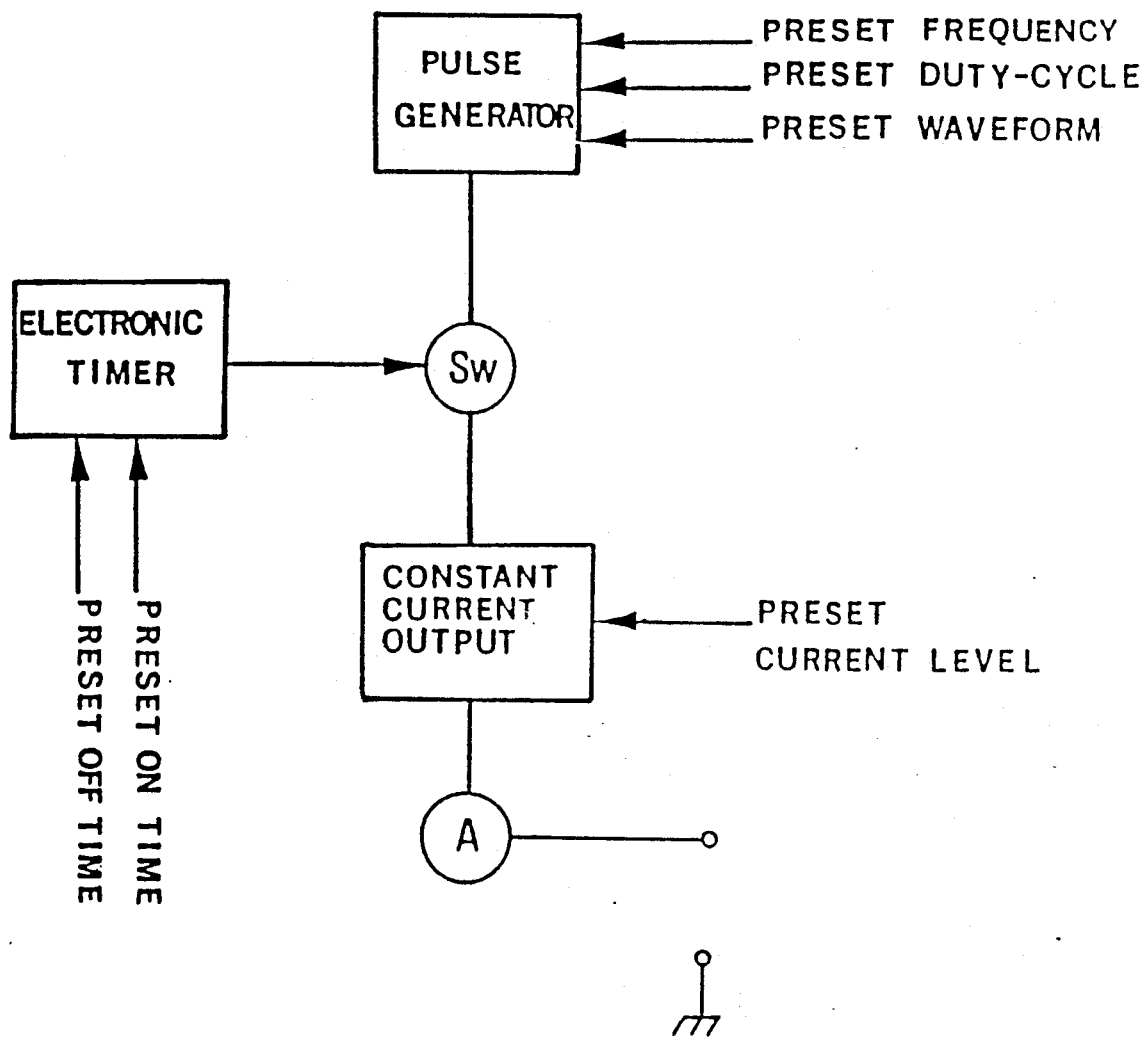
FIG. 12 is a block diagram of a multichannel transdermal periodic iontotherapeutic device coming within the invention.

FIG. 12 is a block diagram of a multichannel transdermal periodic iontotherapeutic device coming within the invention.

Figure 13:
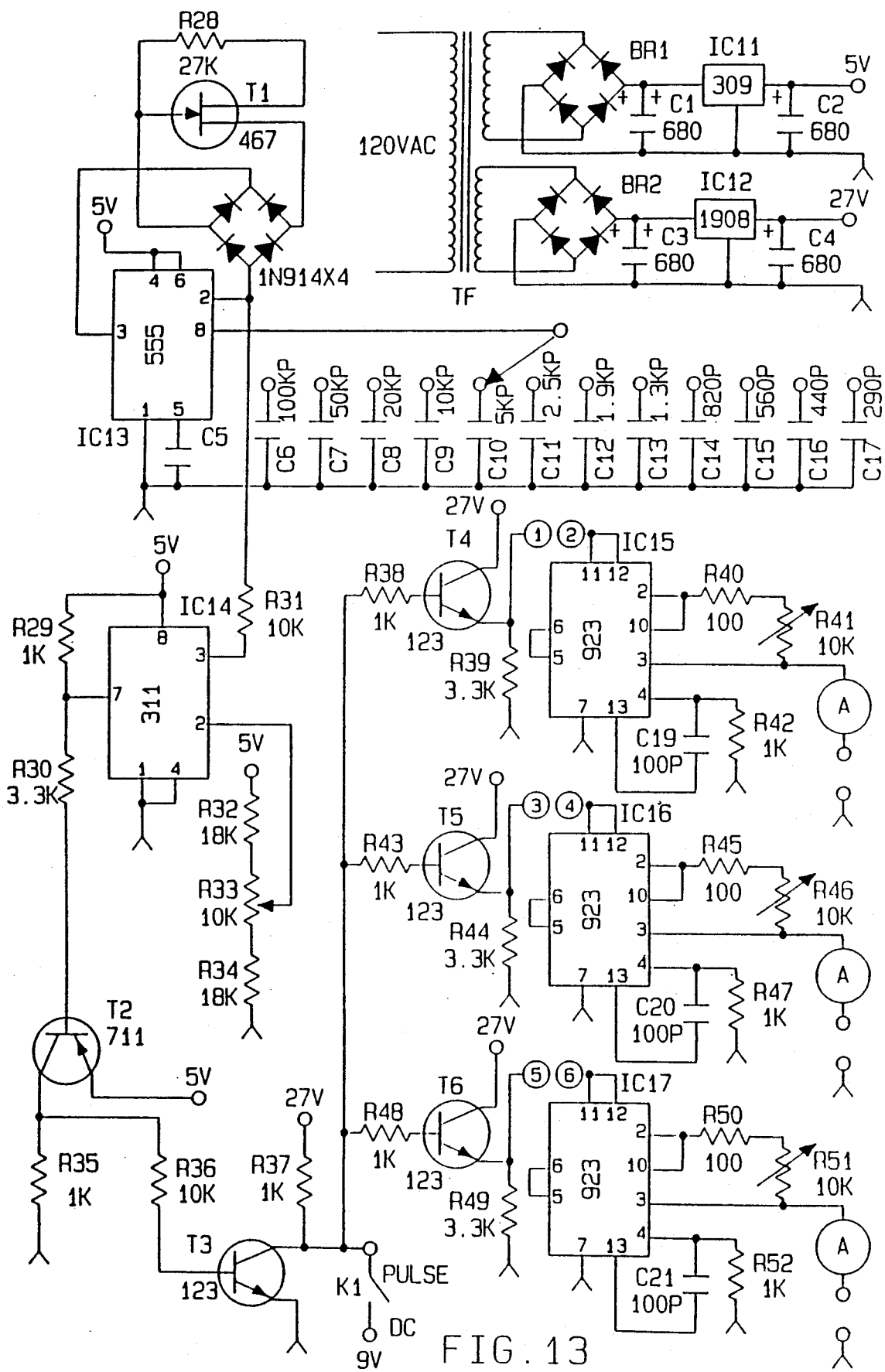
FIG. 13 is a detailed circuit diagram of the device shown in FIG. 12.
Figure 13A:
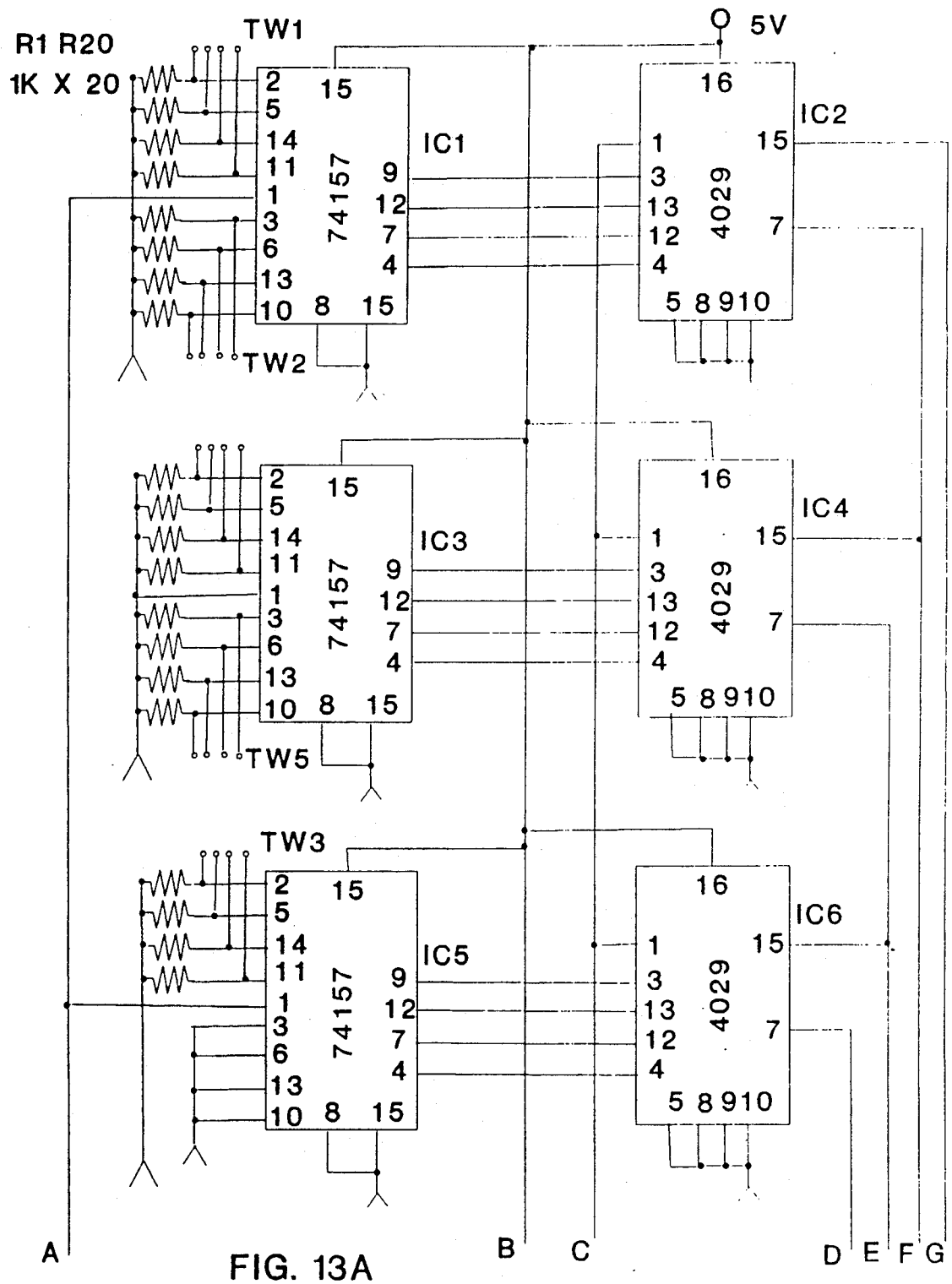
Figure 13B:
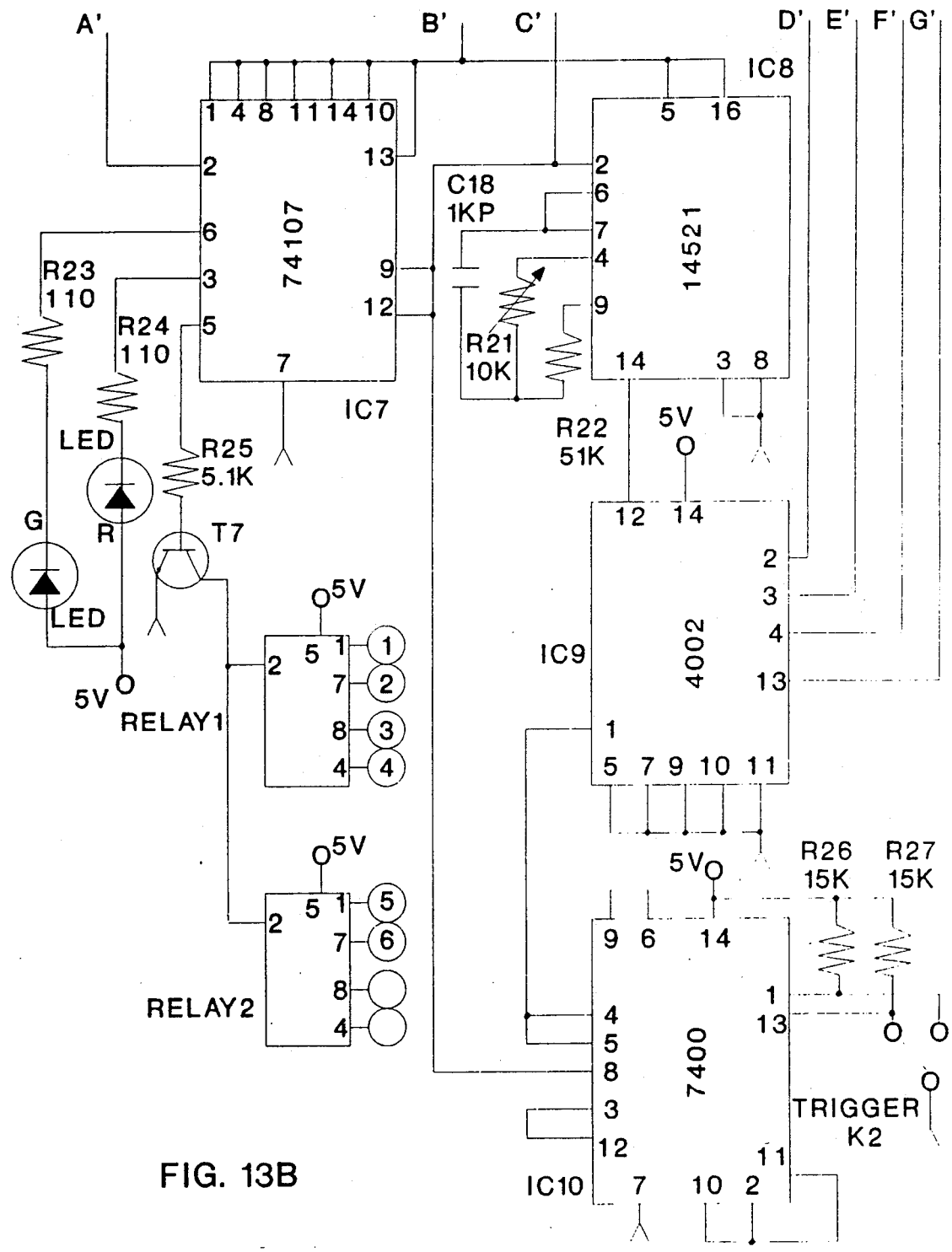

FIG. 13 is a detailed circuit diagram for the multichannel transdermal periodic iontotherapeutic device shown in the block diagram of FIG. 12. Referring to FIG. 13, the following is a description of the circuit, and their functioning:

Power supply

120 V AC line power is stepped down by the transformer TF and rectified by diode bridge $BR_1$ and $BR_2$, respectively. The DC voltages are filtered by capacitors $C_1$, $C_2$ and $C_3$, $C_4$, and fed into voltage regulators $IC_{11}$ and $IC_{12}$, respectively. The output of $IC_{11}$ provides a 5 V supply and the output of $IC_{12}$ provides a 27 V supply.

Timer

The timer consists of ten IC chips, two relays and other components, $IC_8$ provides a system clock. $IC_1$, $IC_3$ and $IC_5$ are quad 2-input multiplexers which consist of four 2-input multiplexers with common select and enable inputs. When the select input is at logical "o", the four output pins assume the values of inputs of pin 1, 5, 14, 11, otherwise, inputs of pin 3, 6, 13, 10. The inputs of the first group represent the "off" time of the timer which has a maximum value of 999 minutes. The inputs of the second group represent the "on" time of the timer which has a maximum value of 99 minutes. The values of both "on" and "off" time needed are set through BCD thumbwheels.

$IC_2$, $IC_4$ and $IC_6$ are "decade-down" counters which receive preset values from multiplexers. The pin 15's of these counters will become logical "o" when the minimum count is reached. When all three counters reach the minimum, $IC_9$, a "AND" gate, will turn to be logical "1". This pulse is inverted by $IC_{10}$ and goes to reset the system clock, reloads counters and converts $IC_7$, which consists of two Flip-Flop's. At the instant when "on" time is finished, the pin 3 and pin 5 turn to be logical "o", which opens two relays and turns on the red LED. At the same time, the pin 2 and pin 6 turns to be logical "1", which will load the values representing the "on" time to pin 4, 7, 9, 12 of three multiplexers and turns off the green LED. At the instant when "off" time is finished, the pin 3 and pin 5 turn to be logical "1", which will load the values representing the "off" time to pin 4, 7, 9, 12 of three multiplexers and turns on the green LED. The whole cycle of both "on" and "off" is repeated for any desired length of time. The switch $K_2$ is used to interrupt the operation and trigger the timer.

Pulse generator and constant current output stages $IC_{13}$, diode bridge consisting of four $IN_{914}$, $T_1$, $R_{28}$ and $C_5$–$C_7$ are components of a triangle wave generator. In this circuit, the charge and discharge currents for one of $C_6$–$C_{17}$ come through the diode bridge formed by four $IN_{914}$, which serve to steer current in the proper direction through the current source made up of $T_1$ and $R_{28}$.

The pin 3 of $IC_2$ serves as a source of current for the timing network, and its state of high or low determines the direction of current flow into or out of the capacitor for charge of discharge. Since both charge and discharge currents flow through the same current regulator circuit, the currents are equal and thus times of charge and discharge are equal. As a result, triangular waves are formed across the working capacitor C.

The circuit covers the frequency range of about 10 $H_z$ to 30 $KH_z$. The adjustment of the frequency is done by the selection of the proper capacitor through a multi-stop switch. The frequency of the triangle-waves can be expressed as $$f \cong \frac{1}{5R_{28}C}$$

The output of the triangle-wave generator is sent to the pin 3 of $IC_{14}$ which serves as a comparator. The voltage comparison is made between pin 2 and pin 3 of $IC_{14}$. The square waves are formed at pin 7 of $IC_{14}$ with a duty cycle which is determined by the voltage-divider composed of $R_{32}$–$R_{34}$. The higher the voltage applied to pin 2 is, the shorter the "on" time of the square waves, and vice versa. The duty cycle of the square waves covers the range of 1/10 to 10/1. The square-waves are amplified by $T_2$ and $T_3$ and then sent to three voltage follower $T_4$–$T_6$.

At the "on" time of the timer, two relays are closed and emitters of $T_4$–$T_6$ are connected to pin 11's of $IC_{15}$–$IC_{17}$. $IC_{15}$–$IC_{17}$ provide three-channel current outputs. Three $IC_{923}$ are employed to serve as current regulators. $IC_{923}$ is originally designed to be a voltage regulator with an output current limit resistor R across pin 10 and pin 3. The maximum current is set as 0.6/R. This feature is adapted to form a current regulator. As soon as the condition $(V_{out}R_L) > I_s$ is satisfied (where $V_{out}$ is the output voltage, $R_L$ load resistance and $I_s$ output current preset), the output current will be kept at the preset level. $R_{40}$, $R_{45}$ and $R_{50}$ are maximum current limit resistance respectively. $R_{41}$, $R_{46}$ and $R_{51}$ are used to preset the desired current. $C_{19}$–$C_{21}$ are used to eliminate high frequency noise.

The output currents are monitored by a current meter A. The switch $K_1$ is used to select DC or pulse output.

Figure 14:
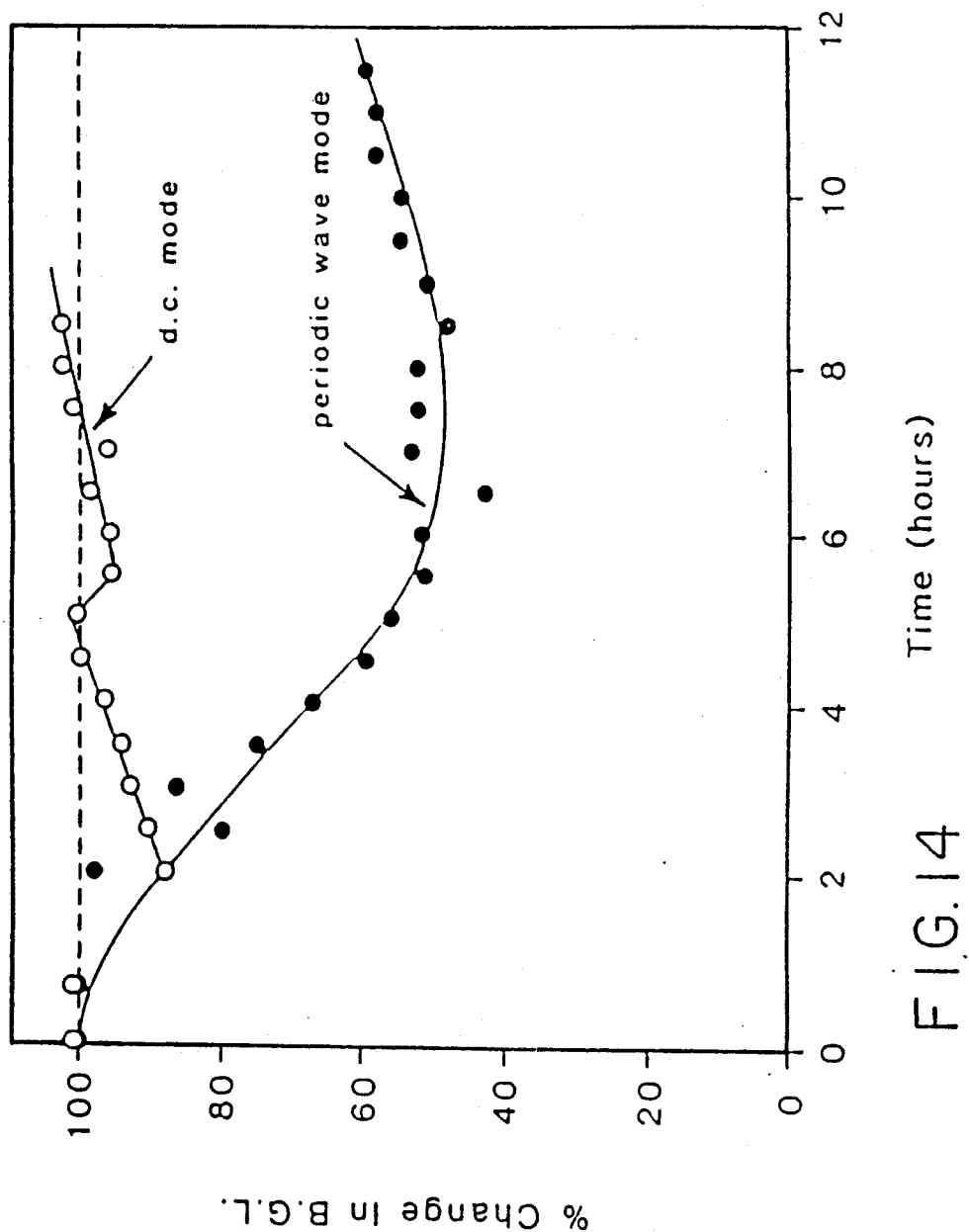
FIG. 14 is a graph comparing the effects of periodic wave mode and DC mode on the transdermal absorption of insulin and on the reduction of blood glucose level (B.G.L.) in the diabetic hairless rats.

FIG. 14 is a graph showing the time course for the reduction of the elevated blood glucose level (% change in B.G.L.) in the diabetic hairless rats as the result of transdermal delivery of insulin from the drug reservoir electrode (containing 250 IU of insulin at pH 7.1) by Transdermal Periodic Iontotherapeutic System for 80 minutes and the effect of current delivery mode. Keys: (O) direct current mode (2 mA), (●) Square-wave periodic mode (2 mA; on/off=4/1; Frequency=2000 Hz).

Figure 15:
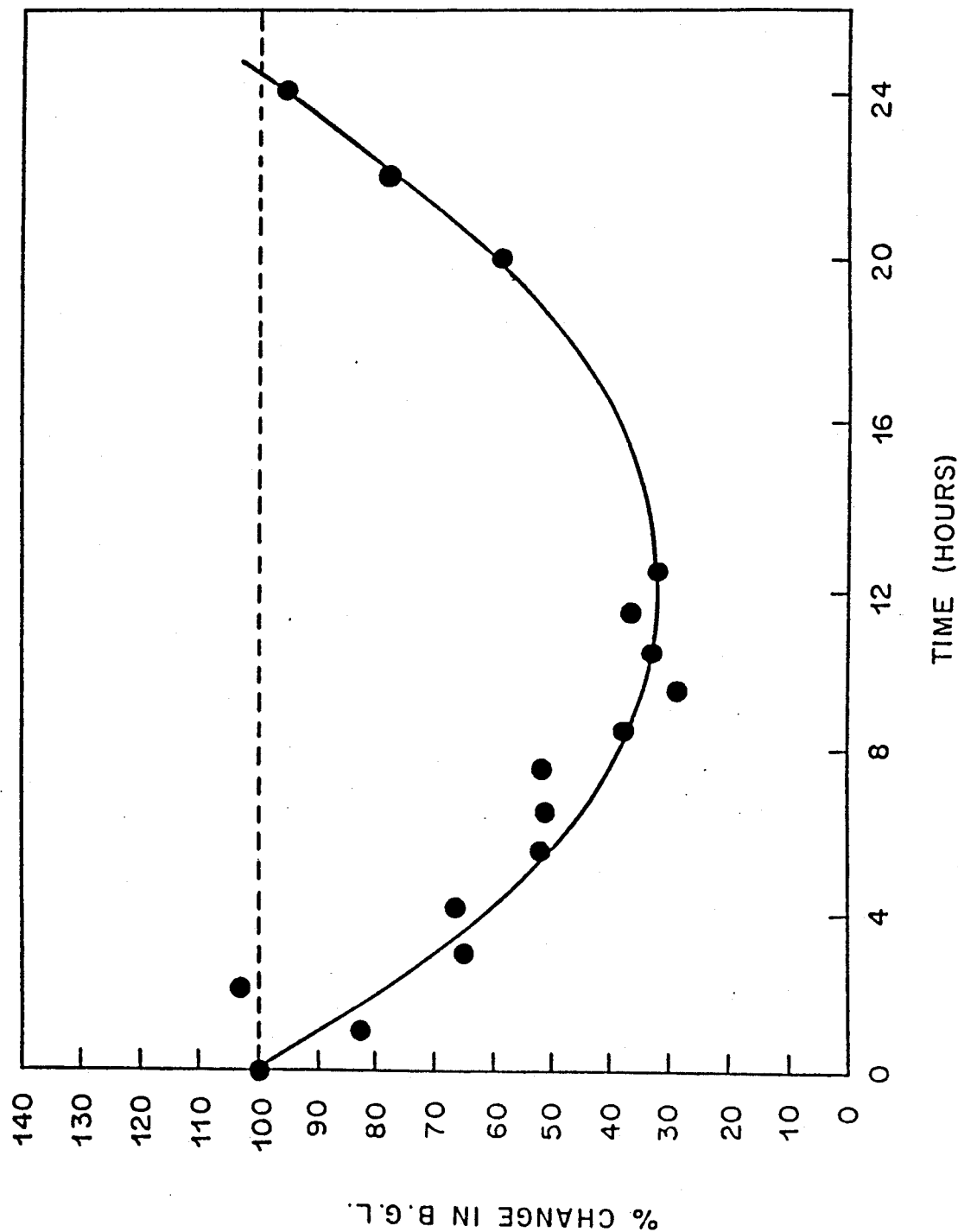
FIG. 15 is a graph showing the time course for the reduction in the blood glucose level (B.G.L.) in the diabetic hairless rats as the result of transdermal delivery of insulin from a pharmaceutical reservoir electrode containing 250 IU of insulin at pH 3.6 by transdermal periodic iontotherapeutic system with square waveform mode (1 mA; on/off=1/1; frequency=2 KHz) for 40 min.

FIG. 15 is a graph showing the time course for the reduction of the elevated blood glucose level (% change in B.G.L.) in the diabetic hairless rats as the results of transdermal delivery of insulin from the pharmaceutical reservoir electrode (containing 250 IU of insulin at pH 3.6) by Transdermal Periodic Iontotherapetic System with square-wave periodic mode (1 mA; on/off=1/1; Frequency=2000 Hz) for 40 minutes.

Figure 16:
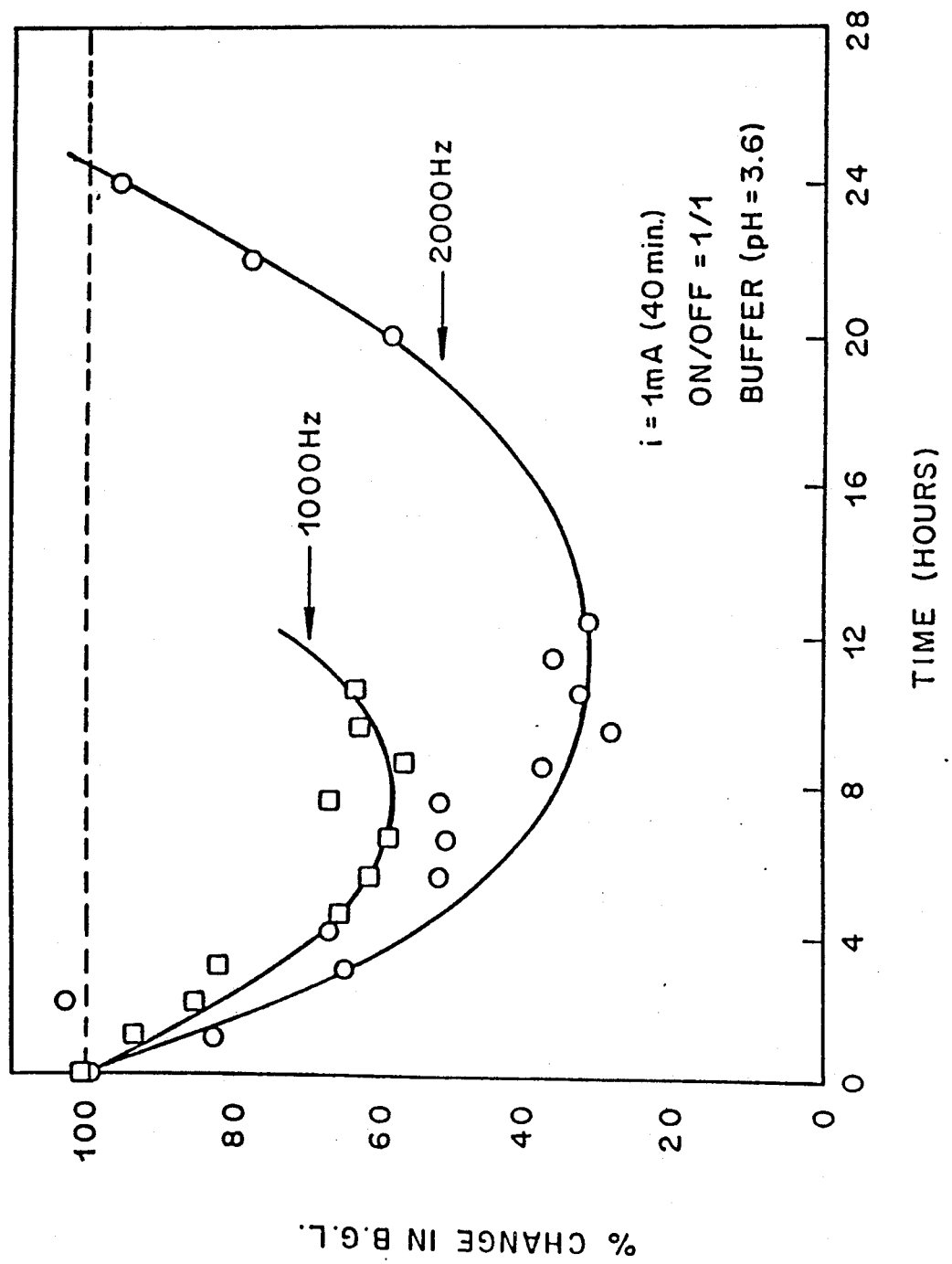
FIG. 16 is a graph showing the effect of the frequency generated by the transdermal periodic iontotherapeutic system on the reduction in the blood glucose level (B.G.L.) in the diabetic hairless rats using insulin.

FIG. 16 is a graph showing the effect of the frequency generated by the Transdermal Periodic Iontotherapeutic System on the reduction of the elevated blood glucose level (% change in B.G.L.) in the diabetic hairless rats. The frequency of 2000 Hz produces a greater magnitude and a longer duration of reduction than the 1000 Hz.

Figure 17:
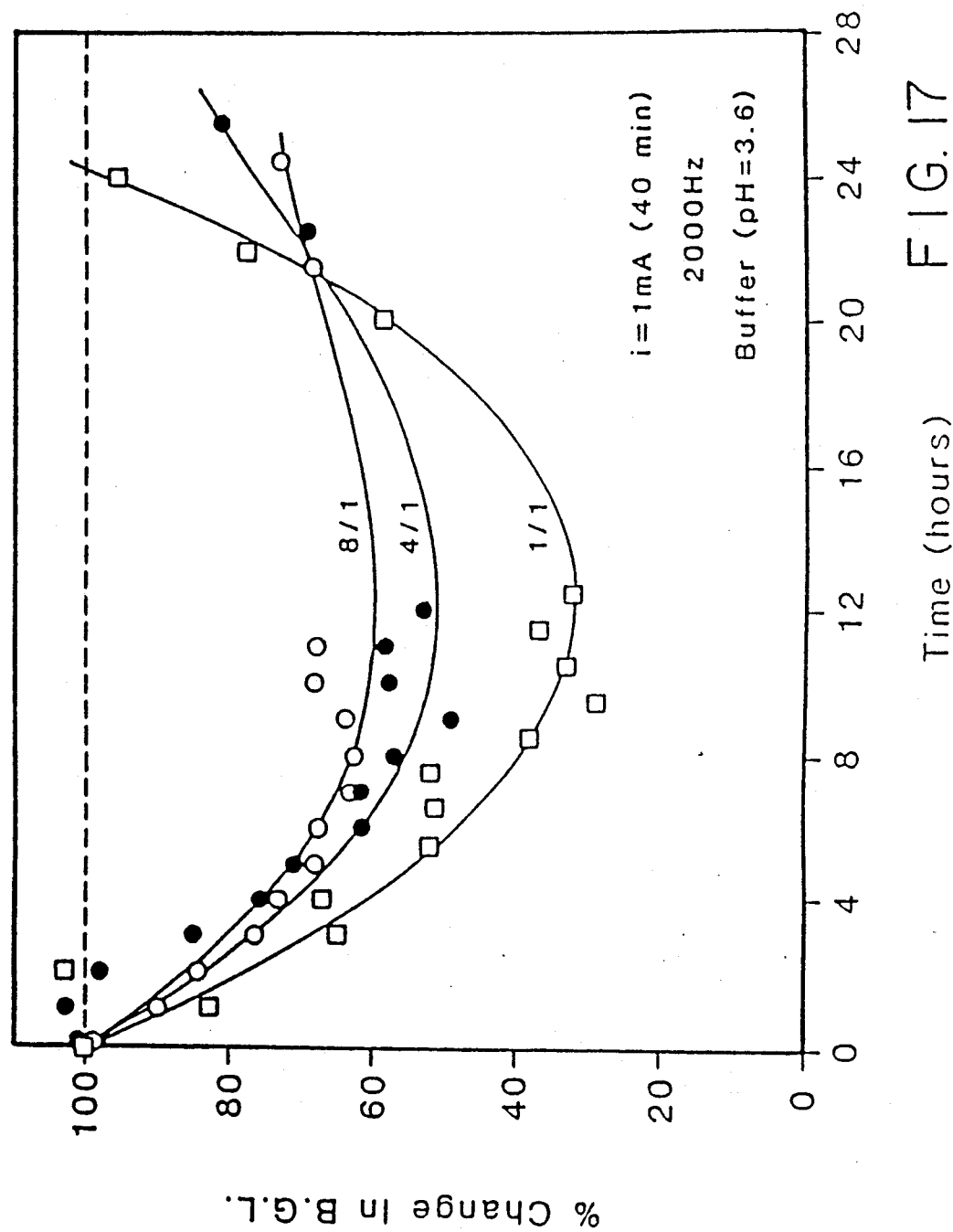
FIG. 17 is a graph showing the effect of the on/off ratio in the transdermal periodic iontotherapeutic system on the reduction in the blood sugar level (B.G.L.) in the diabetic hairless rats using insulin.

FIG. 17 is a graph showing the effect of the on/off ratio in the Transdermal Periodic Iontotherapeutic System on the reduction of the elevated blood glucose level (% change in B.G.L.) in the diabetic hairless rats. By regulating the ratio, the magnitude and the duration of reduction in B.G.L in the diabetes can be controlled as desired.

Figure 18:
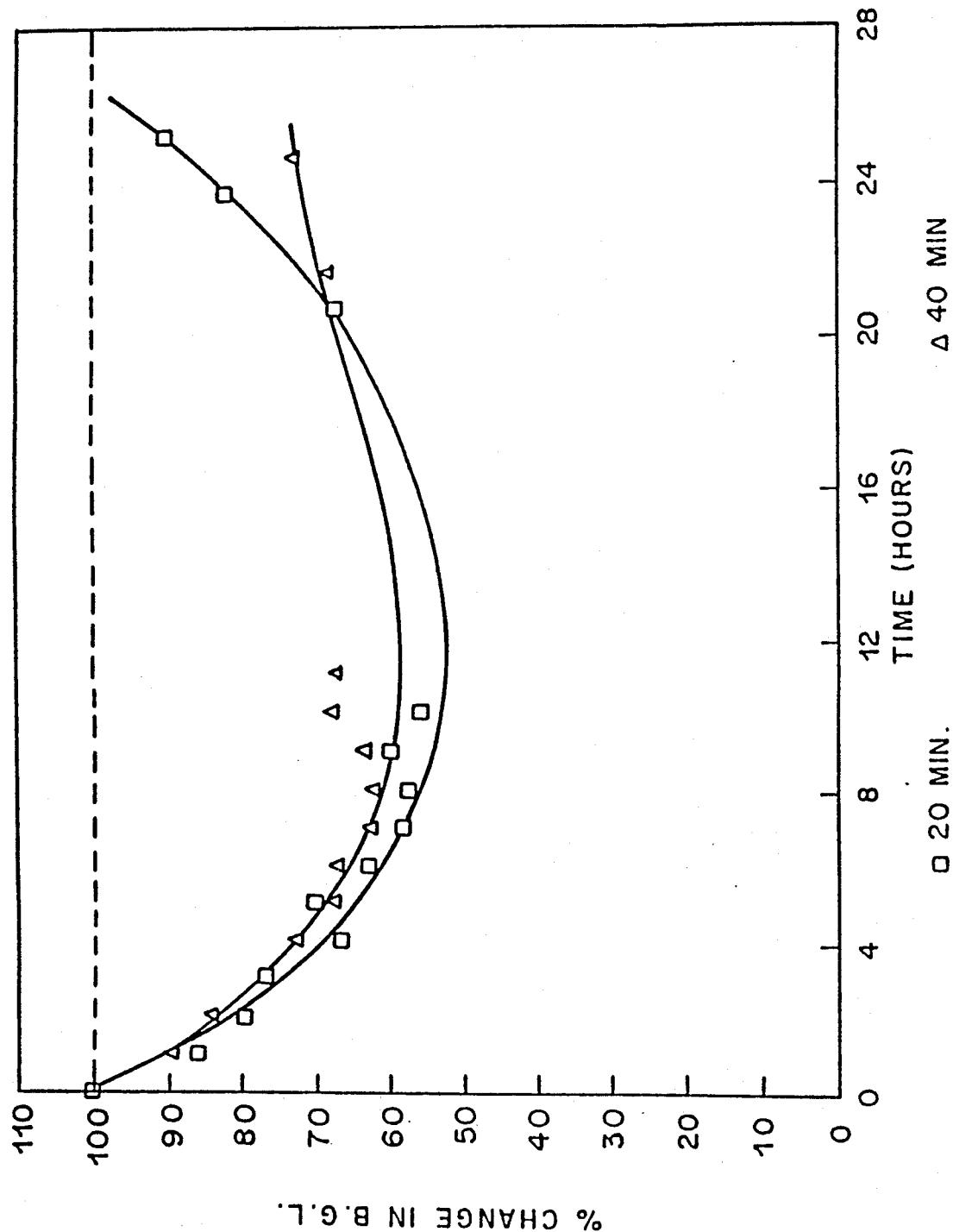
FIG. 18 is a graph showing the effect of the treatment duration by the transdermal periodic iontotherapeutic system with drug reservoir electrode at pH 3.6, on the reduction in the blood glucose level (B.G.L.) in the diabetic hairless rats using insulin.

FIG. 18 is a graph showing the effect of the treatment duration by the Transdermal Periodic Iontotherapeutic System on the reduction of the elevated blood glucose level (% change in B.G.L.) in the diabetic hairless rats. At pH 3.6, which is lower than the isoelectric point of insulin (pH 5.3), with the dose current of 1 mA, on/off ratio of 8/1 and at a frequency of 2000 Hz, the treatment duration of 20–40 minutes appears to be equally effective.

Figure 19:
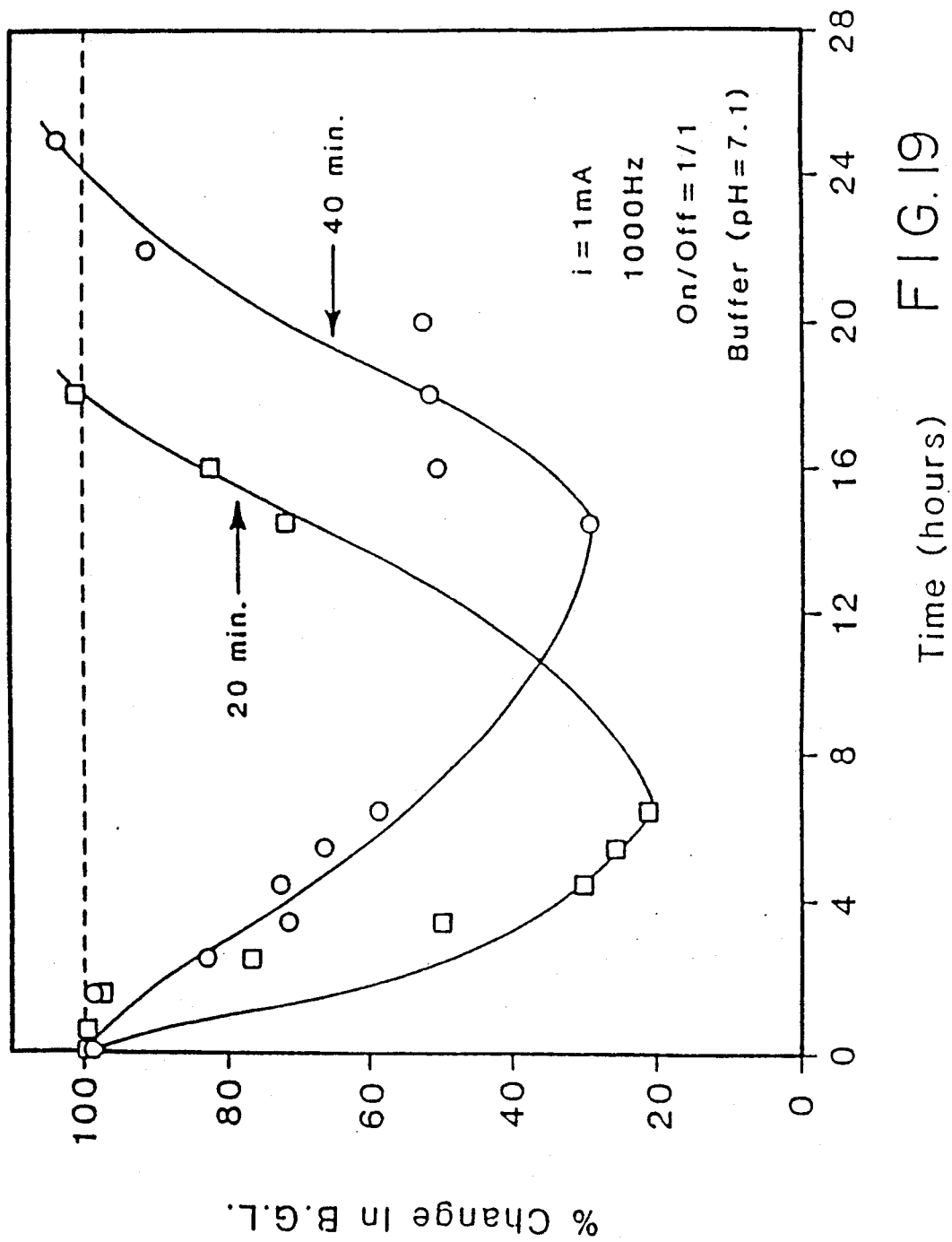
FIG. 19 is a graph showing the effect of the treatment duration by the transdermal periodic iontotherapeutic system, with drug reservoir electrode at pH 7.1, on the reduction in the blood glucose level (B.G.L.) in the diabetic hairless rats using insulin.

FIG. 19 is a graph showing the effect of the treatment duration by the Transdermal Periodic Iontotherapeutic System on the reduction of the elevated blood glucose level (% change in B.G.L.) in the diabetic hairless rats. At pH 7.1, which is higher than the isoelectric point of insulin (pH 5.3), with the dose current of 1 mA, on/off ratio of 1/1 and at frequency of 1000 Hz, the treatment duration produces a difference in the rate and the duration, but with equal effectiveness.

Figure 20:
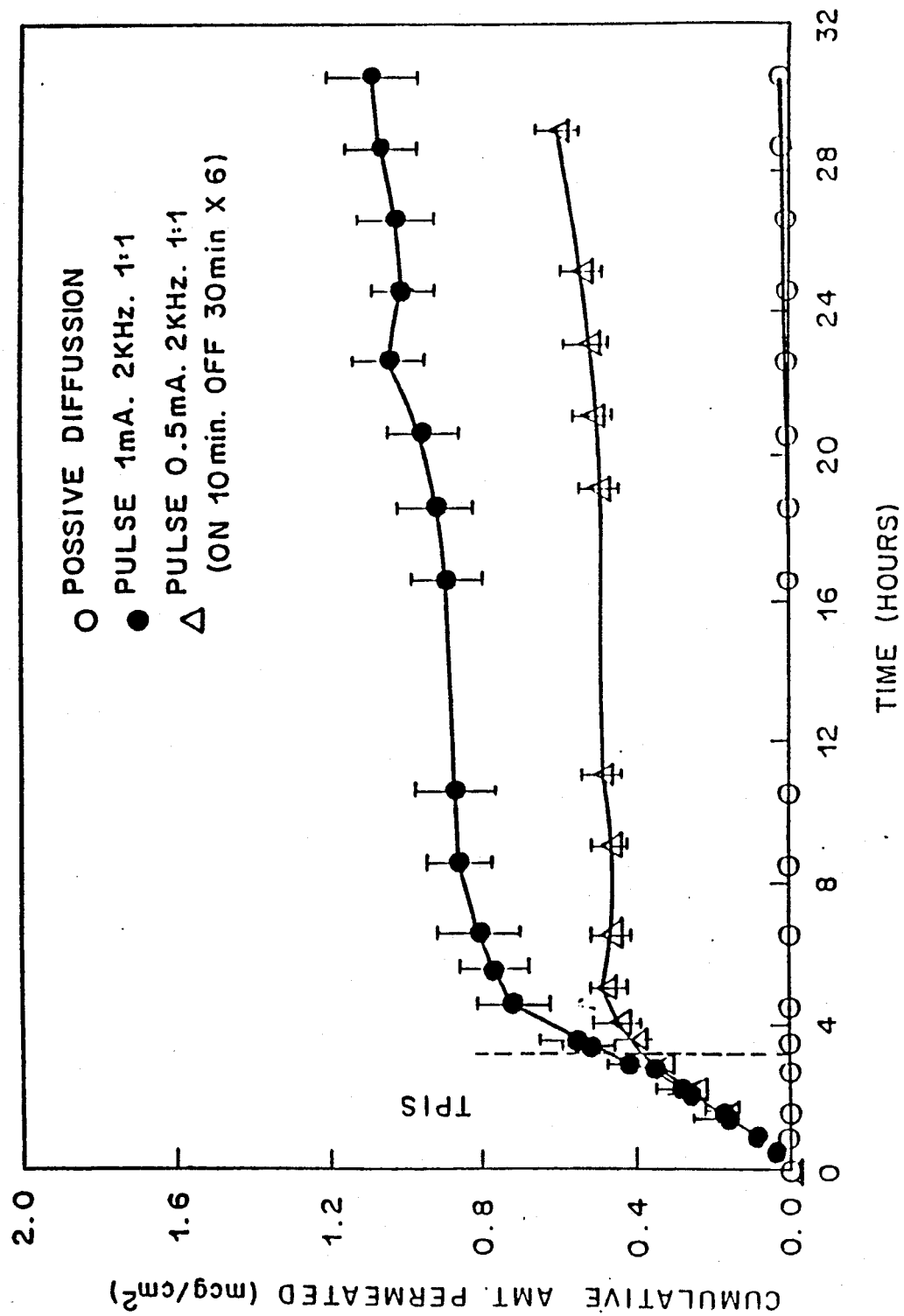
FIG. 20 is a graph showing permeation of vasopressin facilitated by the transdermal periodic iontotherapeutic system compared to passive diffusion of a vasopressin solution at pH 5.0 through hairless rat skin.
Figures 21A, 21B:
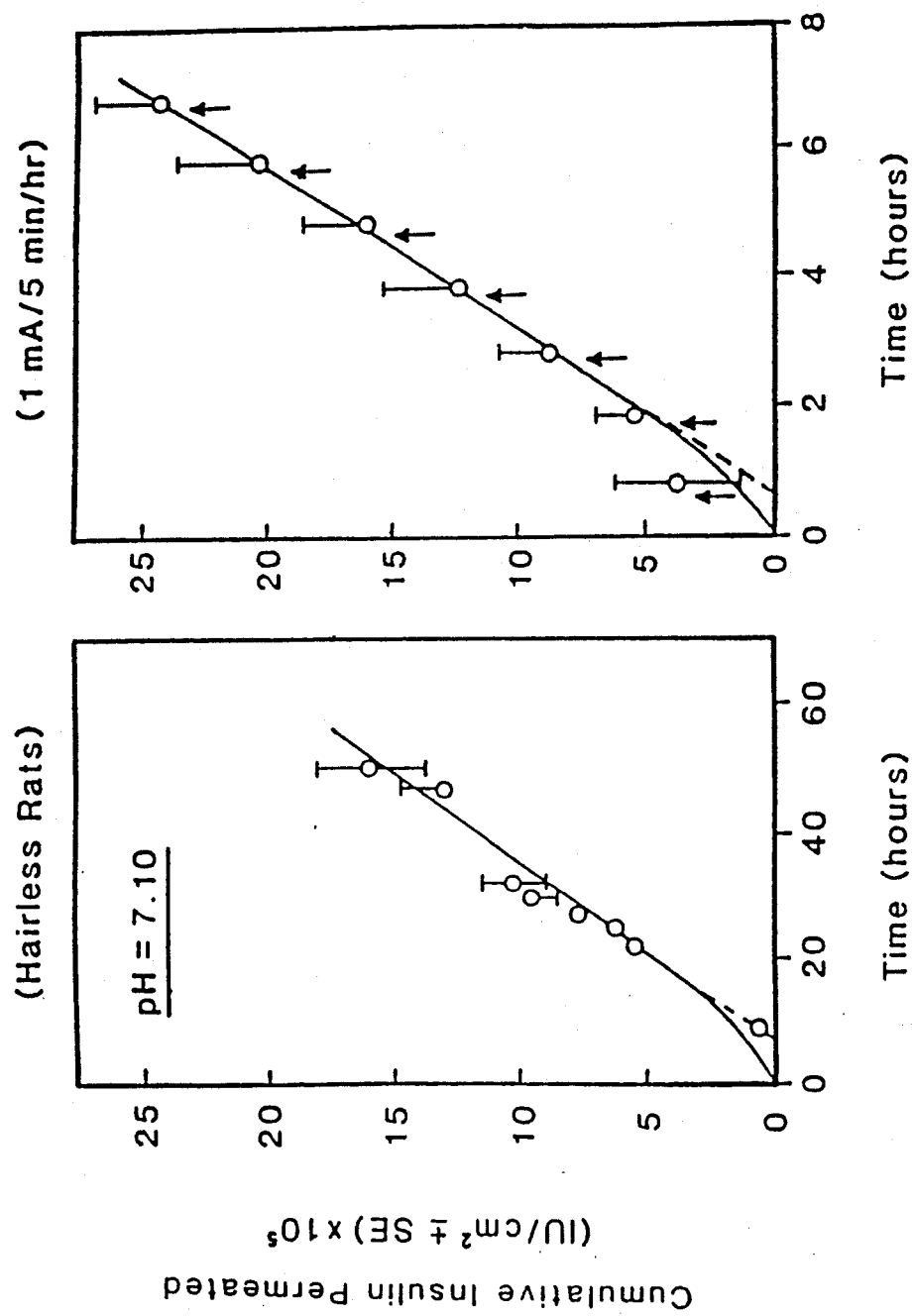
FIG. 21A is a graph showing permeation rate of insulin solution at pH 7.1 through hairless rat skin using no iontotherapy as compared to permeation rate shown in FIG. 21B when using iontotherapy (TIDD).
Figure 22:
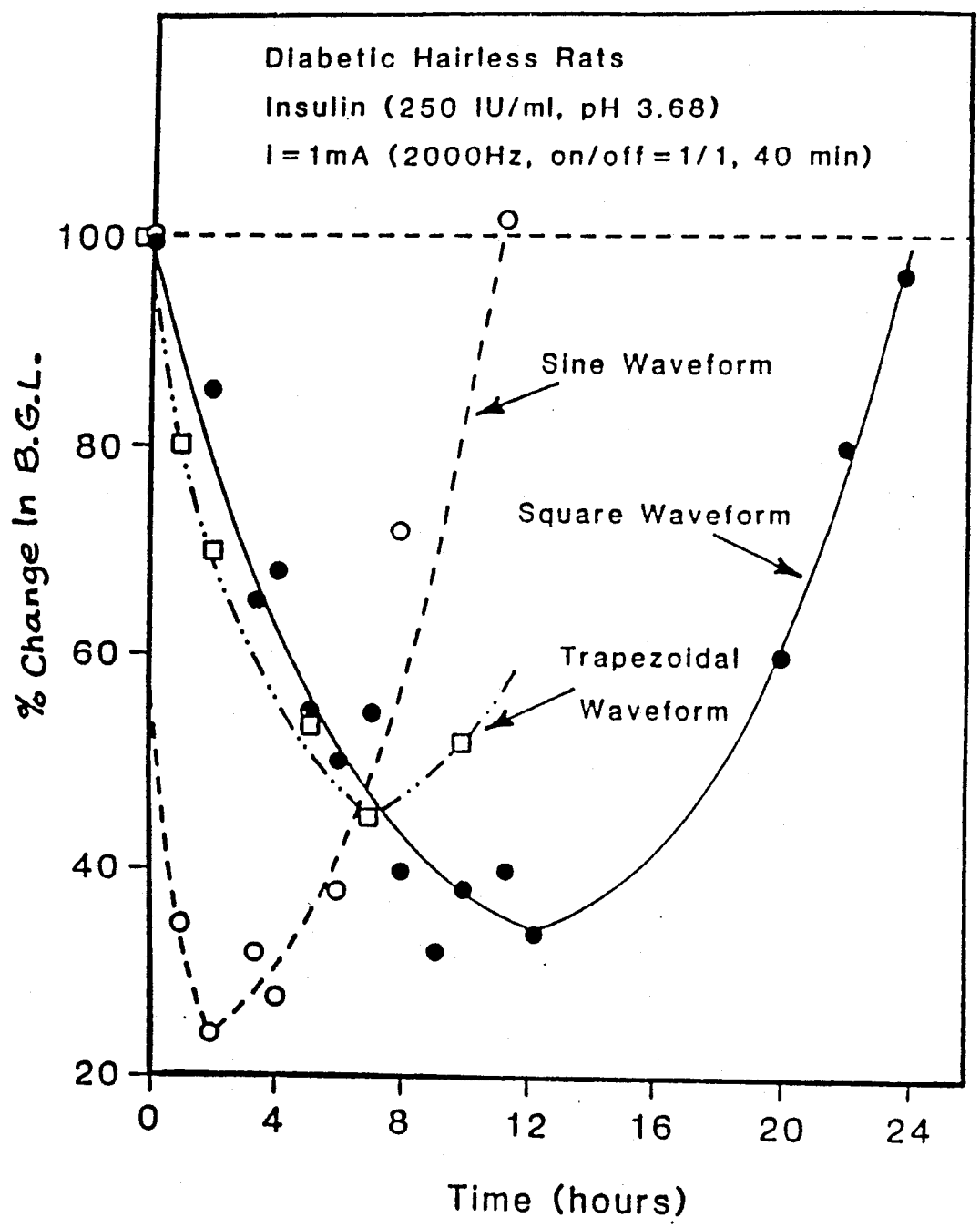
FIG. 22 is a series of graphs showing the comparative effects of the change in waveform in lowering blood glucose level (B.G.L.) in diabetic hairless rats using transdermal periodic iontothorapeutic system using insulin solution at pH 3.68.
Figure 26:
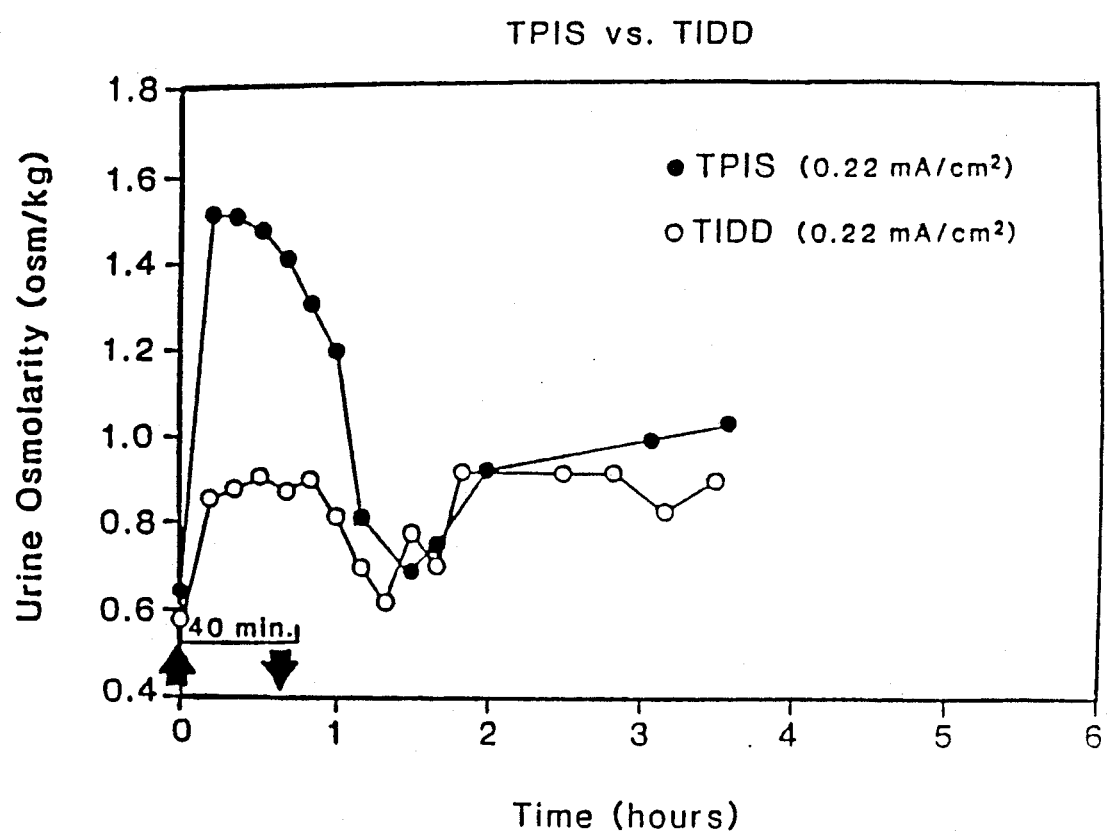
FIG. 26 is a pair of comparative graphs showing a desired reduction in urine output as indicated by urine osmolarity measurement in anesthetized rabbits using transdermal periodic iontotherapeutic system to administer vasopressin solution (pH 5.0). The corresponding graph shows that TPIS is more effective in reducing urine output than TIDD.
Figure 27:
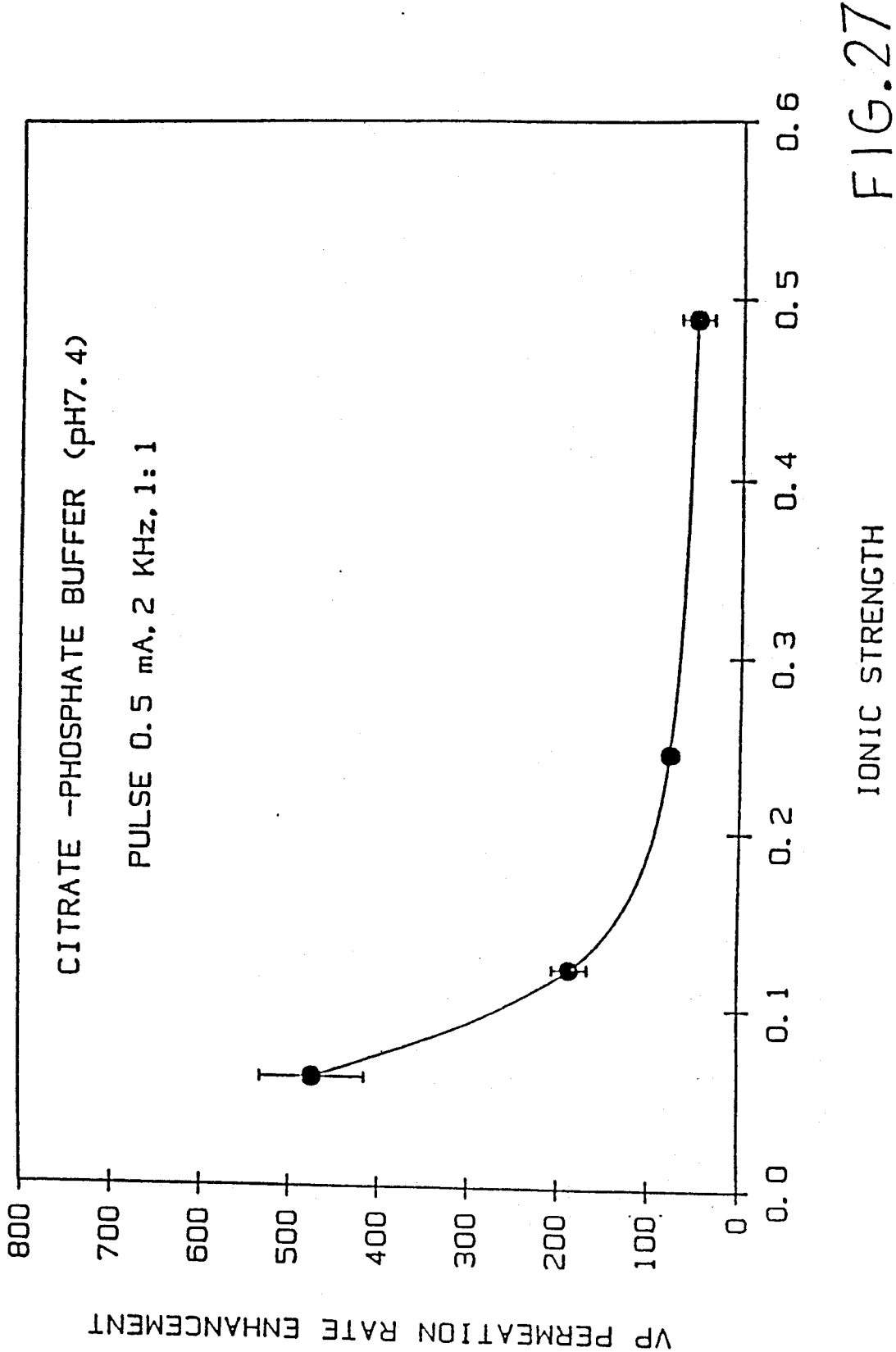
FIG. 27 is a graph showing vasopressin permeation rate enhancement when the ionic strength of the vasopressin solution used in TPIS is decreased.

For a more detailed description of the background for the remaining FIGS., see the indicated Examples: FIG. 20 (Example 11); FIGS. 21A and 21B (Example 12); FIG. 22 (Example 14); FIG. 23 (Example 15); FIGS. 24A and 24B (Example 16); FIG. 25 (Example 17); FIG. 26 (Example 18); FIG. 27 (Example 19); FIG. 28 (Example 20).

In carrying out the iontotherapeutic process for administering transdermally, systemically measured amounts of an ionized pharmaceutical compound, it is first necessary to provide the pharmaceutical-containing unit dose in which the pharmaceutical is in aqueous solution. The pH of the aqueous solution is adjusted to an effective pH either below or above the pKa or the isoelectric point of the pharmaceutical. It is desirable to adjust the pH to an effective level of about 1 pH unit above or below the pKa or isoelectric point of the pharmaceutical, preferably to an effective pH level of at least 1.5 or at least 2 pH units below or above the pKa or isoelectric point of the pharmaceutical. With particular pharmaceuticals, it is preferable to so adjust the pH either below or above the pKa or isoelectric point. For example, with regard to insulins, it is preferable to adjust the pH below the isoelectric point, such as to about 1.0 pH units or lower below the isoelectric point, which for commercial insulins is about pH 5.3.

The formed unit dose is placed in the receptacle portion provided in the pharmaceutical reservoir electrode, so that the ionized pharmaceutical can be transdermally absorbed. If the unit dose form is a preformed self-contained unit dose, it can be held in the receptacle portion of the reservoir electrode by customary means such as clamping, snapping into position, adhesive, or the like.

One convenient form of the unit dose for the ionized pharmaceutical solution is to disperse uniformly the aqueous solution of the ionized pharmaceutical in a polymeric matrix. The polymeric unit dose must be characterized by being able to release the ionized pharmaceutical, when the iontotherapeutic device is in operation, so that the ionized pharmaceutical can be absorbed transdermally. The unit dose is in electrical contact with the skin of the subject treated when the iontotherapeutic device is in operation.

With regard to the unit dose in the form of a polymeric matrix dosage unit, there are a variety of polymers which can be used to make the polymeric matrix unit dose. In general, the polymer must be essentially non-ionic, hyrophilic, and compatible with the ionized pharmaceutical and the skin. The polymer used in making the matrix must permit the ionized pharmaceutical to be released during the operation of the iontotherapeutic device.

Polymers which are suitable in making the matrix are usually referred to as being in the category of hydrophilic polymers or hydrogels. These include the following illustrative cellulose-type and other polymers:
polyhydroxyethylmethacrylate
hydroxypropylcellulose
polyhydroxypropylmethacrylate
hydroxypropylmethylcellulose
polyglycerylmethacrylate
polyacrylamide
polymethacrylamide
polyvinyl alcohol
poly-N-vinyl-2-pyrrolidone In making the polymeric matrix unit doses, certain viscosity-inducing agents may be incorporated to increase the viscosity of the drug reservoir. For example, it has been found suitable to use viscosity-inducing polyethylene glycols. Polyethylene glycols having a molecular weight within the range of 1500 to 8000 are satisfactory. In making the polymeric matrix dosage units, it is suitable to take an amount of a suitable polymer and mix it with water, such as sterile, distilled water, to form a gel. The amount of the polymer used depends upon the type of polymer used and the viscosity imparted to the combination of water and polymer. Sufficient polymer should be used to result in a matrix which retains a sufficient structural integrity during storage and use. It has been found, for example, when hydroxypropylmethylcellulose is used as a matrix-forming polymer, that an amount of about 1.5 to 10%, based upon the amount of water used, is sufficient. It has been found suitable to use about 2% of the hydroxypropylmethylcellulose. Quantities of other polymers used will vary depending upon the type and the molecular weight of the polymer used and the nature of the final matrix disc desired.

The disc is made by first dispersing the polymer, generally referred to as a hydrogel-forming polymer, in water, such as a double distilled and sterile water, or a suitable aqueous solution, such as the aqueous solution of a pharmaceutical. A buffer can be incorporated to maintain a desired pH level. If the desired pH is on the acid side, it has been found acceptable to use a citrate buffer, especially in the pH range of about 3 to 5. If the desired pH is on the basic side, for example, a pH above 7 to about 9, it has been found satisfactory to use a phosphate buffer. It has been found that simple adjustment of the solution pH is satisfactorily carried out, generally speaking, by adding HCl or NaOH, as the case may be. For example, 0.5 molar HCl or NaOH has been found suitable. Other conventional means as known to those skilled in the art can be used to adjust the pH level.

In producing the hydrogel, for example, when hydroxypropylmethylcellulose is employed, the mixture of water and polymer is rapidly stirred to bring about a homogeneous dispersion of the polymer in the water to form a gel. High speed stirrers such as those capable of rotating at 500–1000 rpm, suitably about 600 rpm, can be used. It has been found that any stirring mechanism, including a stirring magnet, can be employed. It is generally desired to carry out the dispersion at slightly elevated temperatures, such as at about 50°–100° C., depending on the polymer used. In producing the dispersion of hydroxypropylmethylcellulose, it has been found that a temperature of about 80° C. is suitable. After the dispersion is produced, it is desirable to continue the stirring during the cooling of the dispersion. The dispersion should be cooled to a temperature slightly above the gelation temperature of the polymer before the pharmaceutical dissolved in water at a suitable concentration is incorporated to form the drug reservoir. In the case of insulin, it has been found that about 2 grams of insulin is satisfactorily dissolved in 100 ml of double-distilled, sterile water and the pH of the insulin solution is desirably adjusted to an acid pH, for example, to a pH of about 3.6 using 0.5 N HCl or other satisfactory acid-pH-adjusting agents. A suitable amount of the acidified insulin solution is added to the dispersion of the polymer in water prior to cooling to the gelation temperature. In the case of insulin, a 2% solution of insulin is a satisfactory concentration to be added to a 2% dispersion of the polymer in water in equal volumes. The material is then suitably cooled in a refrigerator, at about 5° C., to cause a congealing of the insulin-containing polymer dispersion.

It has been found desirable to maintain the ionic strength of the ionized pharmaceutical solutions at a low level, such as not more than about 0.5 or 0.3. It has been found that such low level of ionic strength can provide greater transdermal absorption, such as from peptide solutions, e.g., from vasopressin solutions.

It has been found that the drug-containing polymer discs suitably used with the iontotherapeutic device can be any suitable shape, such as rectangular, circular or square, and the size can range from 5 $cm^2$ to 30 $cm^2$ with a thickness of from about 0.05 to 0.4 cm, a preferred size being up to about 25 $cm^2$ in surface area and about 0.1–0.3 cm in thickness, a more preferred size being 10–20 $cm^2$ in area and 0.1–0.2 cm in thickness. The discs are suitably placed into a properly adapted form-fitting container, which then is aseptically closed as by use of a removable seal to cover the surface of the disc. The formed unit doses then can be placed as required into the receptacle of the reservoir electrode. The unit doses must have means to form electrical contact with the terminus of the lead from the output circuit to the reservoir electrode.

The pharmaceuticals suitable for delivery by this polymer disc can be the anti-diabetic drugs, such as insulins or sulfonyl ureas; the anti-diuretic peptide drugs, such as vasopressin; the calcium-channel blocker-type anti-hypertensive drugs, such as verapamil; the beta-blocker type anti-hypertensive drugs, such as propranolol; narcotic analgesic drugs, such as hydrocodone; non-steroidal anti-arthritic drugs, such as indomethacin; anti-bacterial antibiotics, such as tetracyclines, penicillins and cephalosporins; anti-neoplastic drugs, such as methotrexate; and the peptide hormones, such as luteinizing hormone-releasing hormone (LHRH), oxytocin, and the like.

Pharmaceuticals suitable for use in the process of this invention can be selected from the following or other ionizable pharmaceuticals which are capable of being transdermally absorbed in the iontotherapeutic process, the following systemically-effective pharmaceuticals expected to be capable of delivery by an iontotherapeutic device as developed in this invention: Propranolol HCl, Ibuprofen, Indomethacin HCl, Lorazepam, Thioridazine HCl, Tolazamide, Doxycycline, Flurazepam, Minocycline, Disopyramide, Metoclopromide HCl, Cephalothin sodium, Thiothixene, Vincristine, Oxazepam, Valproic acid, Temazepam, Hydralizine HCl, Ampicillin sodium, Amantadine HCl, Acetohexamide, Haloperidol, Doxepin, Cyclobenzaprine HCl, Sucralfate, Cephalaxin, Cefazolin sodium, Ampicillin, Cefadroxil, Hydralizine HCl, Reserpine and Hydrochlorthiazide, Clindamycin HCl, Carbenicillin disodium, Piroxicam, Fenoprofen calcium, Dialtiazem HCl, Chlorpropamide, Sulindac, Nefedipine, Cimetidine, Naproxen, Piroxicam, Ranitidine HCl, Nadolal, Alprozolam, Captopril, Triazolam, Chlordiazepoxide, Amitryptilline, Dobutamide, Sulfamethoxazole, Trimethoprin, and the like.

The ionizable peptide pharmaceuticals used in the processes and the unit doses of this invention and administered by the devices of this invention are those which are pharmaceutically effective and transdermally absorbable. Desirably the peptides have at least five amino acid units and more desirably at least nine amino acid units.

In operating the process, using for example a wristwatch-type iontotherapeutic device such as provided by this invention, the appropriate unit dose containing the pharmaceutical required for the desired therapy is assembled in the receptacle portion of the pharmaceutical reservoir electrode. For example, if insulin is to be administered and the pH of the insulin solution in the dosage unit is pH 3.6, insulin is a cationic and therefore the dosage unit is assembled as a part of pharmaceutical reservoir electrode, which is the anode. The desired waveform is selected, such as a square waveform. The pharmaceutical reservoir electrode used preferably is adapted to receive a disposable unit dose, e.g., a polymeric matrix unit dose, and to make electric contact with the skin of the subject being treated. Such means is assembled in place. The other variables are selected or pre-selected, such as the frequency, the dose current and on/off ratio. The device is attached to the subject being treated as by a band attached to the device and adapted to be attached to and detached from the subject. The switch of the device is turned to "on" position and the device commences operation of the iontotherapeutic process, which causes the ionized pharmaceutical of reservoir electrode to be administered transdermally and iontotherapeutically to provide a systemic dosing. The particular waveform, mA, pharmaceutical reservoir electrode (i.e., cathode or anode), frequency, length of treatment and other factors will be selected depending upon the pharmaceutical being administered, the subject being treated and others.

Some pharmaceuticals, especially certain relatively low molecular weight pharmaceuticals, can be iontotherapeutically administered using either periodic DC mode or periodic wave mode. For example, the periodic DC mode can be "on" for about 0.5 to about 10 minutes, preferably about 1 to about 5 minutes per hour. During the intervening period during the hour, the device is in "off" position. The "on" period can be more frequent or less frequent, if desired, to provide effective treatment, such as one "on" period every 30 minutes or every ninth minute. In Example 5, it is shown that hydrocodone can be administered following this general procedure. The dose currents, the on/off ratios, the dosage units and the devices described above can be used or adapted to be used in the practice of the periodic DC mode process.

A few hours duration of treatment each day following either procedure is ordinarily adequate, for example, 2 to 10 hours, depending upon factors such as the pharmaceutical, the subject being treated, the iontotherapeutic factors selected and the like.

The following Examples are illustrative of the invention but are not intended to be limiting.

EXAMPLE 1

An aqueous solution of insulin at concentration of 250 IU/ml is prepared by dissolving 96.9 mg (25.8 IU/mg) of pure insulin in 10 ml of double-distilled, sterile water and adjusted to pH 7.1 with 0.5 N NaOH. Two ml of the insulin solution so prepared is filled into a refillable dosage unit having a microporous membrane as the drug-releasing surface. This insulin-containing reservoir-type dosage unit is then assembled as a part of the pharmaceutical reservoir electrode and applied on the abdominal skin of 3 diabetic hairless rats with the transdermal periodic iontotherapeutic system operating at 2 mA with direct current mode or squarewave periodic mode (on/off=4/1; Frequency=2000 Hz). The results on the reduction in blood glucose level are shown and compared in FIG. 14.

EXAMPLE 2

An amount of 200 mg (25.8 IU/mg) of pure insulin is dissolved in 10 ml of double-distilled, sterile water and the pH is adjusted to 3.6 with 0.5 N HCl. An amount of 200 mg of hydroxypropylmethylcellulose is well dispersed in another 10 ml of double-distilled, sterile water using a magnetic stirrer with a stirring bar (5 cm in length) at a rotation speed of 600 rpm. The temperature is controlled at about 80° C. After the hydroxypropylmethylcellulose is dispersed homogeneously, the stirring is continued while the mixture is cooled to about 40° C.

The insulin solution prepared above is then added to the dispersion of hydroxypropylmethylcellulose with intermittent stirring to avoid any denature of insulin molecules, using the same stirring mechanism as described above, at the same stirring rate of 600 rpm for a period of two minutes. The insulin/hydroxypropylmethylcellulose solution is then placed in a refrigerator for congealing to occur. The insulin-containing polymer matrix is cut into disc-shaped parts with the appropriate dimensions, such as 2.5 cm in diameter and 0.2 cm in thickness. The insulin-containing discs are stored at 5° C. The concentration of insulin in the discs is about 250 IU/gm.

The insulin-containing polymeric matrix dosage forms are removed as needed and assembled into the pharmaceutical reservoir electrode. The pharmaceutical reservoir electrode having the insulin-containing polymer unit dose form is the anode since the insulin molecules in the polymeric matrix dose units are cations at pH 3.6, which is lower than the isoelectric point of insulin (pHiso=5.3).

Application of this insulin-containing polymeric matrix unit dose is made onto the abdominal skin of 3 diabetic hairless rats. The transdermal periodic iontotherapeutic system is then operated at 1 mA using an on/off ratio of 1/1, a frequency of 2000 Hz and a square wave mode, for 40 minutes. The result on the reduction in blood glucose level is shown in FIG. 15.

EXAMPLE 3

An aqueous solution of insulin at a concentration of 250 IU/ml is prepared by dissolving 193.8 mg (25.8 IU/mg) of pure porcine insulin in 20 ml of citrate buffer at pH 3.6. Two ml of the insulin solution so prepared is filled into a refillable dosage unit having a microporous membrane as the drug-releasing surface. This insulin-containing reservoir-type dosage unit is then assembled as a part of the pharmaceutical reservoir electrode of the iontotherapeutic device and applied successively on the abdominal skin of 9 diabetic hairless rats with the transdermal periodic iontotherapeutic system operating at 1 mA with square waveform mode to study the effect of frequency, on/off ratio and treatment duration on the reduction of blood glucose level. The results are shown and compared, respectively, in FIGS. 16, 17 and 18.

EXAMPLE 4

The same insulin solution is prepared in the same way as in Example 1, except that a phosphate buffer at pH 7.1 is used to replace the double-distilled water. Two ml of the insulin solution so prepared is filled into a refillable dosage unit having a microporous membrane as the drug-releasing surface. This unit dose is applied to 3 diabetic hairless rats following the same operation procedures as in Example 3 to study the effect of treatment duration on the reduction of blood glucose level. The results are shown in FIG. 19.

EXAMPLE 5

A saturated solution of hydrocodone (pKa=8.56), a narcotic analgesic drug, is prepared in citrate buffer at pH 4.0 and in phosphate buffer at pH 7.5. An aliquot of 3.5 ml of this hydrocodone solution is filled into the reservoir compartment, which is in contact with the stratum corneum surface of the hairless rat abdominal skin, of each Valia-Chien skin permeation cell with the receptor compartment containing equal volume of a pH 7.4 buffered isotonic (drug-free) saline solution. The transdermal periodic iontotherapeutic system is then mounted with its electrodes immersing in the skin permeation cell, one electrode in each of the two solution compartments. A current of 1 mA is applied for 2 min. periodically on the hour for 12 hours at either DC mode or periodic square wave mode (frequency, 2000 Hz; on/off ratio, 1/1). The results are shown in Table I.

TABLE I

Enhancement in Rate and Reduction in Time Lag of the Skin Permeation Rate of Hydrocodone, a Narcotic Analgesic Drug, by the Transdermal Periodic Iontotherapeutic System

| Mode | Skin permeation rate (mcg/cm$^2$/hr $\pm$ S.D.) | | $T_{lag}$ (hrs) |
|---|---|---|---|
| | pH 7.5 | pH 4.0 | |
| Control | 4.75 $\pm$ 1.70 | 3.10 | 5.17 |
| DC mode | 7.61 $\pm$ 2.74 | 37.5 | 0.72 |
| periodic wave mode | 7.01 $\pm$ 1.16 | 59.4 | 0.90 |

EXAMPLE 6

A saturated solution of methotrexate, an anti-neoplastic drug, is prepared in double-distilled water and adjusted to pH 8.0, which is higher than the pKa values of methotrexate (4.8 and 5.5). An aliquot of 3.5 ml of this methotrexate solution (2 mg/ml) is filled into the donor compartment, which is in contact with the stratum corneum surface of the hairless rat abdominal skin, of each Valia-Chien skin permeation cell with the receptor compartment containing equal volume of a pH 7.4 buffered isotonic (drug-free) saline solution. The transdermal periodic iontotherapeutic system is then mounted with its electrodes immersed in the skin permeation cell, one electrode in each of the two solution compartments. A DC current of 1 mA is applied for 10 minutes periodically on the hour for 5 hours with a frequency of 2000 Hz, a square wave form, and an on/off ratio of 4/1. The results are illustrated in Table II:

TABLE II

Enhancing Effect of Transdermal Periodic Iontotherapeutic System (TPIS) on the Skin Permeation of Methotrexate - An Anti-neoplastic Drug

| Time (hrs) | Cumulative Amount of Drug Absorbed (mcg/cm$^2$) | |
|---|---|---|
| | No TPIS | With TPIS |
| 1.33 | 0.0086 | 0.0820 |
| 2.33 | 0.0247 | 0.1373 |
| 3.33 | 0.0471 | 0.4223 |
| 4.16 | 0.0745 | 0.5705 |
| 5.16 | 0.1398 | 1.0835 |

EXAMPLE 7

A saturated solution of propranolol (pKa=9.45), a beta-blocker type anti-hypertensive drug, is prepared in citrate buffer at pH 3.68. The enhancing effect of the transdermal periodic iontotherapeutic system is studied under the same conditions as that outlined in Example 6. The results are shown in Table III:

TABLE III

Enhancing Effect of Transdermal Periodic Iontotherapeutic System (TPIS) on the Skin Permeation of Propranolol[1] - An Anti-hypertensive Beta-Blocker Drug

| Time (hrs) | Cumulative Amount of Drug Absorbed (mcg/cm$^2$) | |
|---|---|---|
| | No TPIS | With TPIS[2] |
| 1.5 | 0.0691 | 0.5970 |
| 2.5 | 0.2615 | 1.6950 |
| 3.5 | 0.5845 | 3.3650 |
| 4.5 | 0.9955 | 5.2150 |

TABLE III-continued

Enhancing Effect of Transdermal Periodic
Iontotherapeutic System (TPIS) on the Skin Permeation
of Propranolol[1] - An Anti-hypertensive Beta-Blocker Drug

| Time | Cumulative Amount of Drug Absorbed (mcg/cm$^2$) | |
|---|---|---|
| (hrs) | No TPIS | With TPIS[2] |
| 5.5 | 2.0800 | 9.0700 |

[1] In the Valia-Chien skin permeation cell, a donor solution containing 13.3 mg/ml of propranolol (pKa = 9.45) at pH 3.68 was applied topically to hairless rat skin at 37° C.
[2] TPIS applied a DC current of 1 mA periodically at 10 min/hr, a frequency of 2000 Hz and an on/off ratio of 4/1.

EXAMPLE 8

A saturated solution of verapamil (pKa=8.9), a calcium-channel blocker-type anti-hypertensive drug, is prepared in citrate buffer at pH 3.68. The enhancing effect of the transdermal periodic iontotherapeutic system is studied under the same conditions as that outlined in Example 6. The results are shown in Table IV:

TABLE IV

Enhancing Effect of Transdermal Periodic
Iontotherapeutic System (TPIS) on the Skin Permeation
of Verapamil[1] - A calcium-channel Blocker-type
Antihypertensive Drug

| Time | Cumulative Amount of Drug Absorbed (mcg/cm$^2$) | |
|---|---|---|
| (hrs) | No TPIS | With TPIS[2] |
| 1.42 | <0.0001 | 0.297 |
| 2.42 | <0.0001 | 0.445 |
| 3.42 | — | 0.695 |
| 4.17 | — | 0.973 |
| 5.17 | <0.0001 | 1.945 |

[1] In the Valia-Chien skin permeation cell, a donor solution containing 23.95 mg/ml of verapamil (pKa = 8.9) at pH 3.68 is applied topically to hairless rat skin at 37° C.
[2] TPIS applied a DC current of 1 mA periodically at 10 min/hr, a frequency of 2000 Hz and an on/off ratio of 4/1.

EXAMPLE 9

A saturated solution of tetracycline HCl (pKa=3.3, 7.8 and 9.7), an antibiotic drug, is prepared in phosphate buffer at ph 9.0. The enhancing effect of the transdermal periodic iontotherapeutic system is investigated under the same conditions as that outlines in Example 6. The results are shown in Table V:

TABLE V

Enhancing Effect of Transdermal Periodic
Iontotherapeutic System (TPIS) on the Skin Permeation:
of Tetracycline HCl[1] - An Antibiotic Drug

| Time | Cumulative Amount of Drug Absorbed (mcg/cm$^2$) | |
|---|---|---|
| (hrs) | No TPIS | With TPIS[2] |
| 1.25 | 0.0180 | 0.1765 |
| 2.25 | 0.0550 | 0.2555 |
| 3.25 | 0.0650 | 0.7815 |
| 4.25 | 0.1450 | 1.3235 |
| 5.25 | 0.3040 | 3.5600 |

[1] In the Valia-Chien skin permeation cell, a donor solution containing 6.2 mg/ml of tetracycline HCl (pKa = 3.3, 7.8 and 9.7) at pH 9.0 is applied topically to hairless rat skin at 37° C.
[2] TPIS applied a DC current of 1 mA periodically at 10 min/hr, a frequency of 2000 Hz, a square waveform and an on/off ratio of 4/1.

EXAMPLE 10

A saturated solution of indomethacin (pKa=4.5), a non-steroidal anti-arthritic drug, is prepared in buffer solution at pH 2.5, which is 2 pH units below the pKa, and at pH 5.5, which is one pH unit above the pKa, and at pH 4.5, the pKa. The enhancing effect of the transdermal periodic iontotherapeutic system is evaluated under the same conditions as that outlined in Example 6. The results are shown in Table VI.

TABLE VI

Enhancing Effect of Transdermal Periodic
Iontotherapeutic System (TPIS) on the Skin Permeation
of Indomethacin - A Non-steroidal Anti-arthritic Drug

| TPIS* | Skin Permeation Rate (mcg/cm$^2$/hr) | | |
|---|---|---|---|
| | pH 2.5 | pH 4.5 | pH 5.5 |
| No | — | — | 1.47 |
| Yes | 0.76 | 0.44 | 6.30 |

*TPIS applied a DC current of 1.2 mA periodically at 5 min/hr, for 7 hours, with a frequency of 2000 Hz, a square waveform and an on/off ratio of 2/1.

EXAMPLE 11

An aqueous buffer solution of vasopressin (50 mcg/ml containing 1.7 mcCi/ml H$^3$-vasopressin) is prepared in citrate-phosphate buffer at pH 5.0. An aliquot of 3.5 ml of this vasopressin solution is filled into the refillable dosage unit having a microporous membrane as the drug-releasing surface. The dosage unit is then assembled as a part of the pharmaceutical reservoir electrode of the iontotherapeutic device and membrane surface thereof is applied to the stratum corneum side of hairless rat skin mounted in the Valia-Chien skin permeation cell at 37° C. Samples are withdrawn at regular intervals and radioactivity is measured by scintillation counter to determine the amount of vasopressin which has been transdermally absorbed.

The results demonstrate that vasopressin permeates through the hairless rat skin at constant, but slow rate for 30 hours (0.94±0.62 ng/cm$^2$/hr) (FIG. 20).

When the skin is treated with transdermal periodic iontophoretic system (TPIS) at current intensity of 0.5 and 1 mA, frequency of 2 KHz, on/off ratio of 1/1, and at the rate of 10 min. per 40 min. for 4 hrs, the skin permeation profiles are enhanced with rate increases from 0.94 (±0.62)ng/cm$^2$/hr (referred to as "passive diffusion" in FIG. 20) to 116.2 (±10.7) and 178.0 (±25)ng/cm$^2$/hr, respectively. After the treatment with transdermal periodic iontophoretic system, referred to in following Table VII as "post-activation phase," the rate of skin permeation of vasopression is reduced to the basal rate of only 0.7 (±0.4) and 5.3 (±0.5)ng/cm$^2$/hr, respectively. The results of the experiment are shown in FIG. 20 and in the following TABLE VII.

TABLE VII

EFFECT OF TPIS ON SKIN
PERMEATION RATE OF VASOPRESSIN

| Conditions | | Skin Permeation[1] (X = SD) | |
|---|---|---|---|
| | Current Intensity | Lag Time (hours) | Rate (ng/cm$^2$ hr) |
| No TPIS | 0.0 mA | 9.12 (± 1.06) | 0.94 (± 0.62) |
| With TPIS | | | |
| (a) Activation phase[2] | 0.5 mA | <0.5 | 116.2 (± 10.7) |
| (b) Post-Activation phase | 0.0 mA | — | 0.7 (± 0.4) |
| (a) Activation phase[2] | 1.0 mA | <0.5 | 178.0 (± 25.0) |
| (b) Post-Activation | 0.0 mA | — | 5.3 (± 0.5) |

TABLE VII-continued

EFFECT OF TPIS ON SKIN PERMEATION RATE OF VASOPRESSIN

| Conditions | Skin Permeation[1] (X ± SD) | |
|---|---|---|
| Current Intensity | Lag Time (hours) | Rate (ng/cm² hr) |
| phase | | |

[1]In-vitro permeation across hairless rate skin mounted in the Valia-Chien permeation cell.
[2]Application of DC at on/off ratio of 1/1 and frequency of 2 KHz, by multi-channel TPIS unit (shown in FIG. 20 for 10 min. per 40 minute period, treatment repeated for six 40-minute cycles.

EXAMPLE 12

An aqueous solution of insulin (5.3 IU/ml containing 0.3 mcCi of I$^{125}$-insulin) is prepared and adjusted to pH 7.1 using NaOH. An aliquot of 3.5 ml of this insulin solution is filled into the refillable dosage unit having a microporous membrane as the drug-releasing surface. The dosage unit is then assembled as a part of the pharmaceutical reservoir electrode of the iontotherapeutic device and membrane surface thereof is applied to the stratum corneum side of hairless rat skin mounted in the Valia-Chien skin permeation cell at 37° C. Samples are withdrawn at regular time intervals and radioactivity is measured by scintillation counter to determine the amount of insulin which has been transdermally absorbed.

The results demonstrate that insulin permeates through the hairless rat skin at constant, but at a slow rate for 48 hours (3.94±0.29 mcIU/cm²/hr) (FIG. 21A).

When the skin is treated with transdermal therapeutic system (TIDD) at current intensity of lmA, frequency of 0 Hz, on/off ratio of 1/1, and at the rate of 5 min. per 60 min. for 7 hrs, the skin permeation profiles are enhanced with rate increased from 3.94 (±0.29) mcIU/cm²/hr to 37.5 (±4.5) mcIU/cm²/hr. FIG. 21B shows comparison of insulin permeation data in FIG. 21A using no iontotherapy (O) over a 7-hr. period with permeation data of same insulin solution using TIDD iontotherapy.

EXAMPLE 13

An aqueous solution of insulin (5.3 IU/ml containing 0.3 mcCi of I$^{125}$-insulin) is prepared and adjusted to pH 3.7, 5.2 or 7.1 using either HCl or NaOH solution. An aliquot of 3.5 ml of this insulin solution is filled into the refillable dosage unit having a microporous membrane as the drug-releasing surface. The dosage unit is then assembled as a part of the pharmaceutical reservoir electrode of the iontotherapeutic device and membrane surface thereof is applied to the stratum corneum side of hairless rat skin mounted in the Valia-Chien skin permeation cell at 37° C. Samples are withdrawn at regular time intervals and radio-activity is measured by scintillation counter to determine the amount of insulin which has been transdermally absorbed.

The results demonstrate that insulin permeates through the hairless rat skin at constant, but rather slow rate for 48 hours, with permeability coefficient ranging from 6.50 (±1.42) to 10.02 (±1.94)×10$^{-7}$ cm/hr (Table VIII). Permeability coefficient is the ratio of the steady state rate of skin permeation of the pharmaceutical which is transdermally absorbed/the concentration of the pharmaceutical solution which is applied transdermally. The pharmaceutical in this experiment is insulin.

When the skin is treated with transdermal iontophoretic system (TIDD) at current intensity of 1 mA, frequency of 0 KHz, on/off ratio of 1/1, and at the rate of 5 min. per 60 min. for 7 hrs, the skin permeation profiles are enhanced with skin permeability coefficient increased to a range from 70.76 (±8.56)×10$^{-7}$ to 242.59 (±18.43)×10$^{-7}$ cm/hr, which show dependence on solution pH. The lower ph solution (pH 3.7) shows greater increase in TPIS-facilitated skin permeability.

TABLE VIII

SKIN PERMEABILITY COEFFICIENT OF INSULIN (Hairless Rats)

| Donor Solution pH | Permeability Coefficient[1] (cm/hr ± SE) × 10$^7$ | |
|---|---|---|
| | No TIDD | With TIDD |
| 3.7 | 6.50 (± 1.42) | 242.59 (± 18.43) |
| 5.2 | 10.02 (± 1.94) | 120.07 (± 22.86) |
| 7.1 | 7.43 (± 0.54) | 70.76 (± 8.56) |

[1]Triplicate Determinations

EXAMPLE 14

An aqueous buffer solution of insulin (250 IU/ml) is prepared in citrate-phosphate buffer at pH 3.68. An aliquot of 2.5 ml of this insulin solution is filled into the refillable dosage unit having a microporous membrane as the drug-releasing surface. The dosage unit is then assembled as a part of the pharmaceutical reservoir electrode of the iontotherapeutic device and membrane surface thereof is applied to the skin at abdominal region of 3 groups of anaesthetized, diabetic hairless rats. Blood samples are withdrawn at regular time intervals and glucose levels are measured by glucose analyzer. The reduction in glucose level from hyperglycemic state is the pharmacodynamic responses to the insulin absorbed transdermally.

The results demonstrate that when the skin is treated with transdermal periodic iontophoretic system (TPIS) at current intensity of 1 mA, frequency of 2 KHz, on/off ratio of 1/1, for 40 min. the blood glucose levels are reduced substantially. The data show that the time course and the extent of reduction in blood glucose levels in diabetic rats vary with the type of waveform used (FIG. 22).

EXAMPLE 15

An aqueous buffer solution of insulin (250 IU/ml) is prepared in citrate-phosphate buffer at pH 3.68. An aliquot of 2.5 ml of this insulin solution is filled into the refillable dosage unit having a microporous membrane as the drug-releasing surface. The dosage unit is then assembled as a part of the pharmaceutical reservoir electrode of the iontotherapeutic device and membrane surface thereof is applied to the skin at abdominal region of 5 anaesthetized, diabetic hairless rats. Blood samples are withdrawn at regular time intervals and glucose levels are measured by glucose analyzer. The reduction in glucose level from hyperglycemic state is the pharmacodynamic responses to the insulin absorbed transdermally.

The results demonstrate that when the skin is treated on Day 1 with transdermal periodic iontophoretic system (TPIS) with insulin in the pharmaceutical reservoir electrode at current intensity of 1 mA, frequency of 2 KHz, square waveform, on/off ratio of 1/1, for 40 min.

the blood glucose levels are reduced substantially (FIG. 23A). On Day 3, the diabetic rats are treated again with TPIS with no insulin in the pharmaceutical reservoir electrode (placebo formulation), the blood glucose are also reduced, indicating that part of the insulin delivered transdermally on Day 1 forms a depot in the skin tissue and can be triggered to be systemically absorbed on Day 3 (FIG. 23B).

EXAMPLE 16

An aqueous solution of insulin (500 IU/ml) at pH 7.10 is used. An aliquot of 2.5 ml of this insulin solution is filled into the refillable dosage unit having a microporous membrane as the drug-releasing surface. The dosage unit is then assembled as a part of the pharmaceutical reservoir electrode of the iontotherapeutic device and membrane surface thereof is applied to the skin at dorsal region of 3 diabetic rabbits. Blood samples are withdrawn at regular time intervals and analyzed for immunoreactive insulin concentration by radioimmunoassay and for glucose levels by glucose analyzer. The reduction in glucose level from hyperglycemic state is the pharmacodynamic responses to the insulin transdermally absorbed.

The results demonstrate that when the skin is treated with transdermal periodic iontophoretic systems (TPIS) at current intensity of 1 mA, frequency of 2 KHz, on/-off ratio of 1/1, and square waveform for 40 min. the plasma immunoreactive insulin concentration increases rapidly and the blood glucose levels are reduced substantially. The plasma insulin profile (FIG. 24A) as well as the time course and the extent of reduction in blood glucose levels (FIG. 24B) in diabetic rabbits are compared with the results from the conventional subcutaneous administration of insulin. The data show that plasma insulin concentrations as well as blood glucose levels can be effectively controlled using TPIS system of this invention. FIG. 24B shows that by using the TPIS system of this inventory the blood glucose level (B.G.L.) can be appropriately reduced in a more controlled manner than by daily SC dosages so as to prevent B.G.L. to fall below normal levels.

EXAMPLE 17

An aqueous solution of insulin (500 IU/ml) at pH 7.10 is used. An aliquot of 2.5 ml of this insulin solution is filled into the refillable dosage unit having a microporous membrane as the drug-releasing surface. The dosage unit is then assembled as a part of the pharmaceutical reservoir electrode of the iontotherapeutic device and membrane surface thereof is applied to the abdominal skin of 2 groups of diabetic rabbits. Blood samples are withdrawn at regular time intervals and analyzed for immunoreactive insulin concentration by radioimmunoassay and for glucose levels by glucose analyzer. The reduction in glucose level from hyperglycemic state is the pharmacodynamic responses to the insulin transdermally absorbed.

The results demonstrate that when the skin is treated with transdermal periodic iontophoretic system (TPIS) at current intensity of lmA, frequency of 2 KHz, on/off ratio of 1/1, and square waveform for 40 min., the the plasma immunoreactive insulin concentration increases more rapidly and the blood glucose levels are reduced more instantaneously than transdermal iontophoretic delivery (TIDD) at current intensity of 4 mA for 80 min. (FIG. 25). The data in FIGS. 25A and B show that the TPIS system of this invention provides both a more rapid increase in plasma insulin concentration after administration and a more rapid reduction in blood glucose level than use of TIDD even though the corresponding current intensity in the TIDD system is 4 times as much (4 mA vs. 1 mA) and administration is 2 times as great (80 minutes vs. 40 minutes) as in the TPIS system.

EXAMPLE 18

An aqueous buffer solution of vasopressin (40 IU/ml) is prepared in citrate-phosphate buffer at pH 5.0. Vasopressin is an anti-diuretic pharmaceutical, which is used by patients which have an excessive urine output. Vasopressin caused a reduction of urine output and an increase in ion content, such as sodium ion content. Ion content in the urine is determined by using osmolarity measurement. An aliquot of 3.5 ml of this vasopressin solution is filled into the refillable dosage unit having a microporous membrane as the drug-releasing surface. The dosage unit is then assembled as a part of the pharmaceutical reservoir electrode of the iontotherapeutic device and membrane surface thereof is applied to the abdominal skin of 2 groups of anesthetized rabbits. Blood samples are withdrawn and urine samples are collected at regular time intervals and urine osmolarity is measured by osmometer. The increases in osmolarity from the basal level are the pharmacodynamic responses to the vasopressin transdermally absorbed.

The results demonstrate that when the skin is treated with transdernal periodic iontophoretic system (TPIS) at current density of 0.22 mA/cm$^2$, frequency of 2 KHz, on/off ratio of 1/1, and square waveform for 40 min., the urine osmolarity increases from the basal levels more rapidly and substantially than with transdermal iontophoretic delivery (TIDD) under the same experimental conditions (FIG. 26).

EXAMPLE 19

An aqueous buffered solution of vasopressin (50 mcg/ml containing 1.7 mcCi/ml H$^3$-vasopressin) is prepared in citrate-phosphate buffer at pH 7.4 with varying ionic strengths. An aliquot of 3.5 ml of this vasopressin solution is filled into the refillable dosage unit having a microporous membrane as the drug-releasing surface. The dosage unit is then assembled as a part of the pharmaceutical reservoir electrode of the iontotherapeutic device and membrane surface thereof is applied to the stratum corneum side of hairless rat skin mounted in the Valia-Chien skin permeation cell at 37° C. Samples are withdrawn at regular time intervals and radioactivity is measured by scintillation counter to determine the amount of vasopressin which has been transdermally absorbed.

The results demonstrate that vasopressin permeates through the hairless rat skin at constant, but slow rate for 30 hours (1.32±0.38 ng/cm$^2$/hr).

When the skin is treated with transdermal periodic iontophoretic system (TPIS) at current intensity of 0.5 mA, frequency of 2 KHz, on/off ratio of 1/1, and at the rate of 10 min. per 40 min. for 4 hrs, the skin permeation profiles are enhanced with rate increases from 1.32 (+0.38)ng/cm$^2$/hr (referred to as "passive diffusion") to the range of 65.9 (±13.1) to 632.6 (±65.0) ng/cm$^2$/hr, depending upon the ionic strength of vasopressin solution. The results of the experiment are shown in the following TABLE IX.

TABLE IX

EFFECT OF IONIC STRENGTH ON SKIN PERMEATION RATE OF VASOPRESSIN

| Ionic Strength | Skin Permeation Rate[1] (ng/cm$^2$/hr ± SD) | Enhancement Factor[2] |
|---|---|---|
| 0.488 | 65.9 (± 13.1) | 49.9 (± 18.0) |
| 0.244 | 101.4 (± 9.1) | 76.8 (± 6.9) |
| 0.122 | 244.6 (± 26.3) | 185.3 (± 19.9) |
| 0.061 | 632.6 (± 65.0) | 472.8 (± 59.0) |

[1] The rates determined in the activation phase with lag time ranging from 0.48 (± 0.21) to 0.86 (± 0.15) hrs.
[2] Compared to the skin permeation rate of vasopressin by passive diffusion (1.32 ng/cm$^2$/hr.)

The TPIS-facilitated skin permeation rate appears to be dependent upon the ionic strength of drug solution. The lower the ionic strength, the higher the rate of skin permeation and the greater the enhancement in skin permeability (FIG. 27).

EXAMPLE 20

An aqueous buffered solution of vasopressin (50 mcg/ml containing 1.7 mcCi/ml H$^3$-vasopressin) is prepared in citrate-phosphate buffer at pH 5.0 at ionic strength of 0.064. An aliquot of 3.5 ml of this vasopressin solution is filled into the refillable dosage unit having a microporous membrane as the drug-releasing surface. The dosage unit is then assembled as a part of the pharmaceutical reservoir electrode of the iontotherapeutic device and membrane surface thereof is applied to the stratum corneum side of hairless rat skin mounted in the Valia-Chien skin permeation cell at 37° C. Samples are withdrawn at regular time intervals and radioactivity is measured by scintillation counter to determine the amount of vasopressin which has been transdermally absorbed.

The results demonstrate that vasopressin permeates through the hairless rat skin at constant, but slow rate for 30 hours (0.98±0.26 ng/cm$^2$/hr).

When the skin is treated with transdermal periodic iontophoretic system (TPIS) at current intensity of 0.3 mA frequency of 16 KHz, on/off ratio of 1/1, for 60 min., the skin permeation profiles are enhanced with rate increases from 0.98 (±0.26)ng/cm$^2$/hr (referred to as "passive diffusion") to 757.3 (±53.2) ng/cm$^2$/hr (FIG. 28), while the duration of time lag is reduced from 9 hours down to 0.40 (±0.06) hours. The data in FIG. 28 demonstrate the reversibility of skin permeability that in less than 2 hours after the TPIS treatment, the skin permeability returns to the rate before the TPIS treatment. Then, TPIS can be applied again to facilitate the skin permeation of vasopressin.

What is claimed is:

1. A transdermal periodic iontotherapeutic process for administering a controlled and systemically effective amount of a pharmaceutically stable and transdermally absorbable peptide pharmaceutical, by
   (1) assembling a dosage unit containing a pharmaceutically acceptable aqueous solution of said peptide into a receptacle of a reservoir electrode of a transdermal periodic iontotherapeutic system, which electrode is a cathode or anode depending upon whether said peptide is anionic or cationic, said solution having a pH at least about 1.0 pH unit below or above the isoelectric point of said peptide;
   (2) placing the cathode and anode electrodes of said transdermal periodic iontotherapeutic system in electrical contact with the intact skin to be treated; and
   (3) applying to said electrodes an iontotherapeutically effective, periodic DC current of up to about 10 mA based on a reservoir electrode/skin-contacting area of about 5 cm, which DC periodic current is monitored and adjusted as required to maintain a constant current intensity within predetermined minimum and maximum levels, using
      (a) a periodic waveform in the square, triangular, sinusoidal, trapezoidal, or other acceptable geometric form, or combinations thereof,
      (b) a physiologically acceptable repetition frequency of at least about 10 Hz, and
      (c) an on/off ratio of from 1/50 to 10/1;
   said process providing a systemically effective absorption of said peptide pharmaceutical from said solution at a rate of at least 500 percent from that provided by passive diffusion transdermal absorption from said solution during an administration time of at least 2 hours.

2. A process of claim 1 in which the pH of the peptide solution is at least about 1.5 pH units below or above the isoelectric point of said peptide.

3. A process of claim 1 in which the pH of the peptide solution is at least about 2.0 pH units below or above the isoelectric point of said peptide.

4. A process of claim 1 in which the pH of the peptide solution is about 1.5 or about 2.0 pH units below the isoelectric point of the peptide.

5. A process of claim 1 in which the peptide is insulin and the pH of the insulin solution is in the range of about pH 3.0 to pH 4.0.

6. A process of claim 5 in which the pH of the insulin solution is about pH 3.6.

7. A process of claim 1 in which the current intensity is not more than about 5 mA based on a reservoir electrode skin-contacting area of about 5 cm$^2$.

8. A process of claim 1 in which the current intensity is not more than about 2 mA based on a reservoir electrode skin-contacting area of about 5 cm$^2$.

9. A process of claim 1 in which the current intensity is not more than 1 mA based on a reservoir electrode/skincontacting area of about 5 cm$^2$.

10. A process of claim 1 in which the periodic DC current has a square waveform.

11. A process of claim 1 in which the periodic DC current has a triangular waveform.

12. A process of claim 1 in which the periodic DC current has a sinusoisal waveform.

13. A process of claim 1 in which the periodic DC current has a trapezoidal waveform.

14. A process of claim 1 in which the peptide has at least 5 amino acid units.

15. A process of claim 1 in which the peptide has at least 9 amino acid units.

16. A process of claim 15 in which the peptide has 9 amino acid units.

17. A process of claim 16 in which the peptide is vasopressin.

18. A process of claim 1 in which the periodic DC current has an administration time of less than about 1 hr followed by multiple repeats of said periodic DC current administration, said periodic DC current administrations being spaced by intervals which are at least as long as the periodic DC current administration times.

19. A process of claim 18 wherein the solution is an insulin solution having a pH which is at least about 1.5 pH units lower or higher than the isoelectric point of the insulin, the current intensity not more than about 2 mA based on a reservoir electrode skin-contacting surface area of about 5 cm², the administration times are not more than about 40 minutes, and the repetition frequency is at least about 1000 Hz.

20. A process of claim 19 in which the periodic waveform is in the square form.

21. A process of claim 19 in which the periodic waveform is in the triangular form.

22. A process of claim 19 in which the periodic waveform is in the sinusoidal form.

23. A process of claim 19 in which the periodic waveform is in the trapezoidal form.

24. A process of claim 1 in which the solution is an insulin solution having a pH which is at least about 1.5 pH units lower or higher than the isoelectric point of the insulin, said insulin transdermally administered at a rate having a skin permeability coefficient of at least $35 \times 10^{-7}$ cm/hr as measured in the Valia-Chien cell using a current intensity of 1 mA, on/off ratio of 1/1, and a repetition frequency of 2000 Hz.

25. A process of claim 24 in which pH is at least about 1.5 pH units lower than the isoelectric point of insulin.

26. A process of claim 24 in which the pH is about 3.6.

27. A process of claim 1 in which the ionic strength of said solution does not exceed about 0.5.

28. A process of claim 27 in which an ionic strength of said solution does not exceed about 0.3.

29. A process of claim 27 in which the peptide pharmaceutical is an insulin or vasopressin.

30. A sterile unit dose adapted to be removably inserted into the receptacle of a reservoir electrode of a transdermal periodic iontotherapeutic system, said unit dose to be used in electrical contact with intact skin to be iontotherapeutically treated to administer transdermally a systemically effective dose amount of a pharmaceutically effective and transdermally absorbable peptide; said unit dose containing a sterile solution of said peptide having an iontotherapeutically effective and physiologically acceptable pH at least about one pH unit lower or higher than the isoelectric point of said peptide so as to provide said pharmaceutical in ionized form; said solution having low ionic strength; said unit dose adapted to permit said peptide to be released upon application to the reservoir electrode of a periodic DC current using a selected waveform in an iontotherapeutic process.

31. A unit dose of claim 30 in which the pH of the peptide solution is at least about 1.5 pH units above or below the isoelectric point of the peptide.

32. A unit dose of claim 31 in which the peptide is contained and uniformly dispersed in a polymeric matrix disc in which the polymer used in making the matrix disc is essentially non-ionic, hydrophilic and essentially compatible with said peptide and the intact skin to be treated.

33. A unit dose of claim 32 in which the polymer is a cellulose-type polymer.

34. A unit dose of claim 31 in which the peptide is insulin.

35. A unit dose of claim 34 in which the pH is in the range of 3.0 to 4.0

36. A unit dose of claim 34 in which the pH is about 3.6.

37. A unit dose of claim 31 in which the peptide is insulin and the pH is about 3.6.

38. A unit dose of claim 30 in which the peptide is vasopressin.

39. A transdermal periodic iontotherapeutic device for transdermally administering a systemically effective amount of an ionized peptide pharmaceutical comprising (1) a DC power supply capable of providing an iontotherapeutically effective and physiologically acceptable DC current in the range up to about 10 mA;

(2) a periodic waveform generator electrically connected to the DC power supply and having integrated circuitry capable of providing (1) a periodic waveform in the square, triangular, sinusoidal, trapezoidal, or other acceptable geometric form or combination thereof; (2) an on/off ratio of 1/50 to 10/1; and a repetition frequency from about 10 Hz to about 50 KHz;

(3) an output circuit electrically connected to said waveform generator which (1) can provide a periodic DC current in a pre-selected waveform of said forms; (b) monitors current intensity delivered; (c) adjusts and maintains the current intensity within predetermined maximum and minimum levels and (d) delivers the current to a reservoir electrode for iontotherapeutic transdermal administration of said peptide pharmaceutical;

(4) a pharmaceutical reservoir electrode which can be preselected to be either the cathode or the anode depending upon whether the ionized pharmaceutical is anionic or cationic; said electrode having a receptacle adapted to receive a unit dose of said peptide pharmaceutical in which said peptide is in aqueous solution at a pH at least 1.0 pH unit below or above the isoelectric point of said peptide; said electrode with said received unit dose adapted to be placed in electrical contact with the intact skin to be treated iontotherapeutically; said electrode having a terminal to receive for transmission through said unit dose the said periodic DC current and said unit dose adapted to be in electrical contact with said terminal; and (5) receptor electrode adapted to be in electrical contact with the intact skin to be treated and forming with said pharmaceutical reservoir electrode a combination of anode and cathode electrodes;

said electrodes electrically connected to said output circuit and providing when placed upon the skin of a subject being treated a current path through the intervening tissue of the subject being treated.

40. A device of claim 39 in which the DC current is generated in the periodic square waveform by said generator and is transmitted by said output circuit to said electrodes to effect iontotherapy.

41. A device of claim 39 in which the DC current is generated in the periodic triangular waveform by said generator and is transmitted by said output circuit to said electrodes to effect iontotherapy.

42. A device of claim 39 in which the DC current is generated in the periodic sinusoidal waveform by said generator and is transmitted by said output circuit to said electrodes to effect iontotherapy.

43. A device of claim 39 in which the DC current is generated in the periodic trapezoidal waveform by said generator and is transmitted by said output circuit to said electrodes to effect iontotherapy.

44. A device of claim 39 which is portable in size.

45. A device of claim 39 which is portable in size and has means for attachment to the subject being treated iontotherapeutically.

46. A device of claim 39 in which the output circuit is multi-channeled.

47. A device of claim 46 which has multiple pairs of electrodes electrically connected to said output circuit and can be applied to multiple number of subjects being treated iontotherapeutically.

* * * * *